US011028128B2

(12) United States Patent
Eisenberg et al.

(10) Patent No.: US 11,028,128 B2
(45) Date of Patent: Jun. 8, 2021

(54) INHIBITION OF THE AGGREGATION OF TRANSTHYRETIN BY SPECIFIC BINDING OF PEPTIDES TO AGGREGATION-DRIVING SEGMENTS

(71) Applicant: THE REGENTS OF THE UNIVERSITY OF CALIFORNIA, Oakland, CA (US)

(72) Inventors: David S. Eisenberg, Los Angeles, CA (US); Lorena Saelices Gomez, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/313,848

(22) PCT Filed: Jun. 29, 2017

(86) PCT No.: PCT/US2017/040103
§ 371 (c)(1),
(2) Date: Dec. 27, 2018

(87) PCT Pub. No.: WO2018/005866
PCT Pub. Date: Jan. 4, 2018

(65) Prior Publication Data
US 2020/0010507 A1   Jan. 9, 2020

Related U.S. Application Data

(60) Provisional application No. 62/356,971, filed on Jun. 30, 2016, provisional application No. 62/507,081, filed on May 16, 2017.

(51) Int. Cl.
| | |
|---|---|
| *C07K 7/08* | (2006.01) |
| *C07K 7/06* | (2006.01) |
| *G01N 33/68* | (2006.01) |
| *A61K 38/00* | (2006.01) |

(52) U.S. Cl.
CPC .............. *C07K 7/08* (2013.01); *C07K 7/06* (2013.01); *G01N 33/6896* (2013.01); *A61K 38/00* (2013.01); *G01N 2800/28* (2013.01); *G01N 2800/7047* (2013.01)

(58) Field of Classification Search
CPC . C07K 7/08; C07K 7/06; C07K 14/00; G01N 33/6896; G01N 2800/28; G01N 2800/7047; A61K 38/00; A61K 38/16; G06F 16/252; G06F 16/284; G06Q 10/00
See application file for complete search history.

(56) References Cited

U.S. PATENT DOCUMENTS

| | | | |
|---|---|---|---|
| 7,083,948 B1 * | 8/2006 | Sassenfeld ............... | C12P 21/06 435/69.1 |
| 8,754,034 B2 * | 6/2014 | Eisenberg ............... | C07K 7/06 514/1.1 |
| 2014/0056904 A1 | 2/2014 | Chakrabartty et al. | |
| 2015/0037341 A1 | 2/2015 | Lindahl et al. | |
| 2016/0108093 A1 | 4/2016 | Murphy et al. | |

FOREIGN PATENT DOCUMENTS

| | | | | |
|---|---|---|---|---|
| WO | WO2008/063369 | * | 5/2008 | ............. G01N 33/53 |
| WO | 2010042852 A2 | | 4/2010 | |

OTHER PUBLICATIONS

Saelices et al. Uncovering the Mechanism of Aggregation of Human Transthyretin. The Journal of Biological Chemistry, vol. 290, No. 48, p. 28932-28943. (Year: 2015).*
Transthyretin sequesters amyloid beta protein and prevents amyloid formation. PNAS, 1994, vol. 91, pp. 8368-8372. (Year: 1994).*
Cho et al. Transthyretin-Derived Peptides as beta-Amyloid Inhibitors. ACS Chemical Neuroscience. 2014,vol. 5, pp. 542-551. (Year: 2014).*
Sassenfeld et al. A Polypeptide Fusion Designed for the Purification of Recombinant Proteins. Bio/Technology, Jan. 1984, pp. 76-81. (Year: 1984).*
PCT International Search Report & Written Opinion dated Dec. 15, 2017, Application No. PCT/US17/40103.
Anonymous: 11 A3V5K3: Uncharacterized protein, ORFName SKA53_15276 In: "A3V5K3: Uncharacterized protein, ORFName SKA53_15276 ",Jan. 20, 2016, 1 page.
Cruz M et al: Inhibition of beta-amyloid toxicity by short peptides containing N-methyl amino acids11 , Journal Peptide Research, Blackwell Publishing Ltd, Oxford; GB, vol. 63, No. 3, Mar. 1, 2004 (Mar. 1, 2004), pp. 324-328.
Extended European Search Report dated Oct. 2, 2020 for EP Application No. 17821294.0.
Galant et al:, "Substoichiometric inhibition of transthyretin misfolding by immune-targeting sparsely populated misfolding intermediates: a potential diagnostic and therapeutic for TTR amyloidoses", Scientific Reports, vol. 6, No. 1, Apr. 28, 2016 pp. 1-12.
Higaki et al: Novel conformation-specific monoclonal antibodies against amyloidogenic forms of transthyretin11 , AMY LO ID, vol. 23, No. 2, Mar. 16, 2016 (Mar. 16, 2016) , pp. 86-97.

* cited by examiner

*Primary Examiner* — Marcela M Cordero Garcia
(74) *Attorney, Agent, or Firm* — Gates & Cooper LLP

(57) ABSTRACT

The invention disclosed herein relates to peptide inhibitors for transthyretin (TTR) aggregation and methods of inhibiting TTR aggregation, cytotoxicity, and/or TTR amyloidosis. Illustrative embodiments of the invention include a composition of matter comprising at least one peptide designed to inhibit the aggregation of TTR, with this peptide typically being coupled to a heterologous amino acid tag. A pharmaceutically acceptable carrier selected to be compatible with the inhibitory peptide may also be included. A method for blocking or inhibiting the aggregation of transthyretin TTR is also provided. The method comprises combining TTR with an effective amount of an inhibitory peptide or pharmaceutical composition, so that TTR aggregation and/or cytotoxicity is blocked or inhibited.

9 Claims, 5 Drawing Sheets
Specification includes a Sequence Listing.

SEQUENCE LISTING

```
<160> NUMBER OF SEQ ID NOS: 73

<210> SEQ ID NO 1
<211> LENGTH: 147
<212> TYPE: PRT
<213> ORGANISM: Homo sapiens

<400> SEQUENCE: 1

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Phe His Glu His Ala Glu Val Val Phe Thr Ala
1               5                   10

<210> SEQ ID NO 3
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Tyr Ser Tyr Ser Thr Thr Ala Val Val Thr Asn
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Val Ala His Pro Phe Val Glu Phe Thr Glu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Tyr Val Thr Asn Pro Thr Ser Tyr Ala Val Thr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Phe Glu Val Ala Phe Pro Val Glu His Ala Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Val Ser Asn Pro Thr Ser Thr Tyr Val Ala Thr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

```
Val Ala Asn Thr Ser Pro Thr Ser Tyr Tyr Val Thr
1               5                   10
```

```
<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Arg Arg Pro Arg His Glu His Ala Glu Val Val Phe Thr Ala
1               5                   10                  15
```

```
<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Arg Arg Arg Pro Phe Arg Glu His Ala Glu Val Val Phe Thr Ala
1               5                   10                  15
```

```
<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Arg Arg Pro Phe His Arg His Ala Glu Val Val Phe Thr Ala
1               5                   10                  15
```

```
<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Arg Arg Arg Pro Phe His Glu Arg Ala Glu Val Val Phe Thr Ala
1               5                   10                  15
```

```
<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Arg Arg Pro Phe His Glu His Arg Glu Val Val Phe Thr Ala
1               5                   10                  15
```

```
<210> SEQ ID NO 14
<211> LENGTH: 16
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 14

Arg Arg Arg Arg Pro Phe His Glu His Ala Arg Val Val Phe Thr Ala
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 15

Arg Arg Arg Arg Pro Phe His Glu His Ala Glu Arg Val Phe Thr Ala
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 16

Arg Arg Arg Arg Pro Phe His Glu His Ala Glu Val Arg Phe Thr Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 17

Arg Arg Arg Arg Pro Phe His Glu His Ala Glu Val Val Arg Thr Ala
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 18

Arg Arg Arg Arg Pro Phe His Glu His Ala Glu Val Val Phe Arg Ala
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 19

Arg Arg Arg Arg Pro Phe His Glu His Ala Glu Val Val Phe Thr Ala
1               5                   10                  15

```
<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Arg Arg Pro Arg Ser Tyr Ser Thr Thr Ala Val Val Thr Asn
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Arg Arg Arg Pro Tyr Arg Tyr Ser Thr Thr Ala Val Val Thr Asn
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Arg Arg Pro Tyr Ser Arg Ser Thr Thr Ala Val Val Thr Asn
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Arg Arg Arg Pro Tyr Ser Tyr Arg Thr Thr Ala Val Val Thr Asn
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Arg Arg Pro Tyr Ser Tyr Ser Arg Thr Ala Val Val Thr Asn
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25
```

Arg Arg Arg Arg Pro Tyr Ser Tyr Ser Thr Arg Ala Val Val Thr Asn
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Arg Arg Pro Tyr Ser Tyr Ser Thr Thr Arg Val Val Thr Asn
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Arg Arg Pro Tyr Ser Tyr Ser Thr Thr Ala Arg Val Thr Asn
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Arg Arg Pro Tyr Ser Tyr Ser Thr Thr Ala Val Arg Thr Asn
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Arg Arg Pro Tyr Ser Tyr Ser Thr Thr Ala Val Val Arg Asn
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Arg Arg Pro Tyr Ser Tyr Ser Thr Thr Ala Val Val Thr Asn
1               5                   10                  15

<210> SEQ ID NO 31
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 31

Arg Arg Arg Arg Val Glu His Ala Val Glu Ala His Phe Thr Phe Pro
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Arg Arg Ala Phe Glu Ala His Val His Thr Glu Phe Val Pro
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Arg Arg Arg Glu His His Phe Phe Glu Ala Val Val Ala Thr Pro
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Arg Arg Arg Glu His Val Ala His Phe Phe Val Glu Thr Pro Ala
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Arg Arg Arg Glu His Val Phe Val His Glu Phe Ala Thr Pro Ala
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Arg Arg Pro Glu Phe Glu Val Ala Ala Val Phe His Thr His
1               5                   10                  15
```

```
<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Arg Arg Arg Pro Phe Ala Ala Val Phe His Val Glu Glu His Thr
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Arg Arg Arg His Ala Glu Val Phe Val Glu His Ala Pro Thr Phe
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Arg Arg Arg His His Ala Phe Ala Val Phe Glu Val Pro Thr Glu
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: N-me-A

<400> SEQUENCE: 40

Arg Arg Arg Arg Pro Phe His Glu His Ala Glu Val Val Phe Thr Ala
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Arg Arg Arg Phe Val His Val Thr Ala Phe Glu Pro Ala His Glu
1               5                   10                  15

<210> SEQ ID NO 42
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 42

Arg Arg Arg Arg Glu His Ala His Val Phe Ala Val Pro Thr Phe Glu
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Arg Arg Arg Phe Pro Ala Val Thr Ala Phe Glu His Val Glu His
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Arg Arg Arg Glu Val Pro His Val Ala His Ala Glu Phe Phe Thr
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Arg Arg Arg Glu Phe Thr Val Glu Ala Phe Pro His Ala His Val
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Arg Arg Arg His Val Ala His Pro Phe Val Glu Phe Thr Glu Ala
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: N-me-E

<400> SEQUENCE: 47
```

Arg Arg Arg Arg His Val Ala His Pro Phe Val Glu Phe Thr Glu
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: N-me-E

<400> SEQUENCE: 48

Arg Arg Arg Arg His Phe Glu Ala Phe Pro Glu His Val Val Ala Thr
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: N-me-E

<400> SEQUENCE: 49

Arg Arg Arg Arg His Phe Glu Val Ala Phe Pro Val Glu His Ala Thr
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: N-me-A

<400> SEQUENCE: 50

Arg Arg Arg Arg Asn Val Thr Thr Ser Tyr Tyr Thr Val Ala Ser Pro
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Arg Arg Arg Ala Val Ser Val Ser Tyr Thr Tyr Thr Asn Pro Thr
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic

```
                           peptide

<400> SEQUENCE: 52

Arg Arg Arg Arg Asn Thr Ala Tyr Ser Val Val Thr Ser Thr Pro Tyr
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Arg Arg Arg Thr Thr Ala Tyr Ser Thr Asn Val Ser Tyr Pro Val
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Arg Arg Arg Pro Ala Thr Tyr Asn Ser Thr Ser Val Val Thr Tyr
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Arg Arg Arg Thr Asn Val Tyr Tyr Ser Thr Ala Val Pro Thr Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Arg Arg Arg Pro Tyr Ala Val Asn Tyr Thr Ser Thr Ser Thr Val
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Arg Arg Arg Thr Tyr Ala Asn Thr Val Tyr Ser Thr Pro Val Ser
1               5                   10                  15

<210> SEQ ID NO 58
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Arg Arg Arg Pro Tyr Ser Tyr Ser Thr Thr Ala Val Val Thr Asn
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Arg Arg Arg Ser Ala Ser Thr Tyr Tyr Val Thr Pro Asn Val Thr
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Arg Arg Arg Tyr Val Pro Thr Thr Val Ala Tyr Asn Ser Ser Thr
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Arg Arg Arg Val Thr Ser Pro Thr Ala Val Ser Tyr Thr Tyr Asn
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Arg Arg Arg Thr Ser Tyr Pro Asn Ser Val Thr Thr Ala Tyr Val
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63
```

Arg Arg Arg Arg Ser Tyr Tyr Val Pro Val Ser Thr Thr Asn Thr Ala
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: N-me-A

<400> SEQUENCE: 64

Arg Arg Arg Arg Tyr Val Ser Asn Pro Thr Ser Thr Tyr Val Ala Thr
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Arg Arg Arg Ser Tyr Val Thr Asn Pro Thr Ser Tyr Ala Val Thr
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N-me-A

<400> SEQUENCE: 66

Arg Arg Arg Arg Val Ala Asn Thr Ser Pro Thr Ser Tyr Tyr Val Thr
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Arg Arg Arg His Val Ala His Pro Phe Val Glu Phe Thr Glu
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Arg Arg Arg Ser Tyr Val Thr Asn Pro Thr Ser Tyr Thr Val

-continued

```
1               5                   10                  15

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Arg Arg Arg
1

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: N-me-E

<400> SEQUENCE: 70

Arg Arg Arg Arg Pro Phe His Glu His Ala Glu Val Val Phe Thr Ala
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: N-me-A

<400> SEQUENCE: 71

Arg Arg Arg Arg Pro Tyr Ser Tyr Ser Thr Thr Ala Val Val Thr Asn
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: N-me-E

<400> SEQUENCE: 72

Arg Arg Arg Arg His Val Ala His Pro Phe Val Glu Phe Thr Glu
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (14)..(14)
<223> OTHER INFORMATION: N-me-A

<400> SEQUENCE: 73

Arg Arg Arg Arg Ser Tyr Val Thr Asn Pro Thr Ser Tyr Ala Val Thr
1               5                   10                  15
```

US 11,028,128 B2

INHIBITION OF THE AGGREGATION OF TRANSTHYRETIN BY SPECIFIC BINDING OF PEPTIDES TO AGGREGATION-DRIVING SEGMENTS

CROSS-REFERENCE TO RELATED APPLICATIONS

This application claims priority under Section 119(e) from U.S. Provisional Application Ser. No. 62/356,971, filed Jun. 30, 2016, and U.S. Provisional Application Ser. No. 62/507,081, filed May 16, 2017, both entitled "INHIBITION OF THE AGGREGATION OF TRANSTHYRETIN BY SPECIFIC BINDING OF PEPTIDES TO AGGREGATION-DRIVING SEGMENTS" the contents of each which are incorporated herein by reference.

SEQUENCE LISTING

The instant application contains a Sequence Listing which has been filed electronically in ASCII format and is hereby incorporated by reference in its entirety. Said ASCII copy, created on Jun. 12, 2020, is named 30435_0316USWO-_SL.txt and is 22,428 bytes in size.

TECHNICAL FIELD

The invention relates to inhibitory peptides, and in particular the inhibition of transthyretin aggregation.

BACKGROUND OF THE INVENTION

Each amyloid disease is characterized by the aggregation of a particular protein into amyloid fibrils. Amyloid fibrils have the capacity to serve as seeds that induce further aggregation of the parental protein. Transthyretin (TTR) is a 55 kDa tetrameric protein that transports retinol binding protein (RBP) and thyroxine (T4) in the blood and cerebrospinal fluid. Amyloid aggregation of TTR occurs by dissociation of tetrameric TTR into monomers; these partially unfold into amyloidogenic intermediates, and self-associate into soluble oligomers and amyloid aggregates. Familial point mutations are known to destabilize the tetramer, leading to a faster dissociation and consequent amyloid aggregation.

Two diseases are associated with amyloidosis of TTR (ATTR). Wild-type amyloidosis is a late-onset disease in which wild type (WT) TTR aggregates weaken the heart muscle. WT ATTR is usually diagnosed post-mortem in patients over 80 years old. In addition, TTR-related neuropathy or cardiomyopathy cases are often hereditary conditions, grouped as hereditary amyloidoses, fatal disorders characterized by a extracellular deposition of TTR amyloid fibrils in a variety of tissues such as kidneys, eye, gastrointestinal tract, and skin. Some of the most detrimental deposits are in the heart and peripheral nerves. Hereditary amyloidotic polyneuropathies include a set of mutations, such as L55P and V30M, which result in progressive sensorimotor and autonomic neuropathy. Hereditary amyloidotic cardiomyopathies include the mutation D38A and cause protein deposition in heart tissue.

Unfortunately, there is no cure for transthyretin-related amyloidoses, although one drug is approved for European use and various therapeutics are currently in clinical trials. Thus, there is still a great need for compositions and methods of inhibiting transthyretin aggregation and preventing/reducing transthyretin-related amyloidosis.

SUMMARY OF THE INVENTION

As noted above, TTR aggregation is linked to transthyretin amyloidosis, a condition that is not yet curable. Although new strategies are being evaluated, the development of combinatory systems to tackle various processes during TTR aggregation is desirable in order to maximize treatment options. As disclosed herein, amyloid seeds extracted from hearts of ATTR patients robustly seed wild type transthyretin into amyloid fibrils and this seeding is not inhibited by compounds previously shown to stabilize the native structure of transthyretin. Importantly however, seeding is inhibited by designed inhibitors which cap fibril growth, both in vitro and in *Drosophila* ATTR models. Using this discovery, compositions and methods of aggregation inhibition are provided herein, ones directed towards targeting segments of TTR that are necessary for protein aggregation and are exposed only when the TTR tetramer dissociates.

The invention disclosed herein has a number of embodiments. One embodiment of the invention is a composition of matter comprising at least one inhibitory peptide that inhibits transthyretin (SEQ ID NO: 1) aggregation by binding to residues 22 to 48 (strands B and C), residues 86 to 97 (strand F), or residues 113 to 124 (strand H) of transthyretin. In such embodiments of the invention, at least one of the amino acids in the inhibitory peptide comprises a non-natural amino acid; and/or the inhibitory peptide is coupled to a heterologous peptide tag (e.g. a sequence of amino acid residues that facilitates the solubility, stability, detection etc. of the inhibitory peptide sequence to which the tag is coupled). In typical embodiments of the invention, the inhibitory peptide comprises an inhibitory peptide having an amino acid sequence shown in Table 1 below, optionally with a heterologous peptide tag such as the poly arginine peptide tag (RRRR (SEQ ID NO: 69)) shown in this Table. Optionally the composition comprises a plurality of such inhibitory peptides.

In an illustrative embodiment of the invention, at least one inhibitory peptide comprises the sequence: PFHEHAEVVFTA (SEQ ID NO: 2); PYSYSTTAVVTN (SEQ ID NO: 3); HVAHPFVEFTE (SEQ ID NO: 4); SYVTNPTSYAVT (SEQ ID NO: 5); HFEVAFPVEHAT (SEQ ID NO: 6); YVSNPTSTYVAT (SEQ ID NO: 7); or VANTSPTSYYVT (SEQ ID NO: 8), where at least one of the amino acids in the inhibitory peptide comprises a non-natural amino acid; and/or the inhibitory peptide is coupled to a heterologous peptide tag. Optionally for example, the inhibitory peptide comprises a D-amino acid; or an amino acid comprising a non-naturally occurring N-methyl group moiety. In embodiments of the invention where the inhibitory peptide is coupled to a heterologous peptide tag, this tag can comprise an amino acid sequence that increases peptide solubility; and/or an amino acid sequence that facilitates monitoring or manipulation of the peptide. In typical embodiments of the invention, the inhibitory peptide is from 6 to 30 amino acids in length.

Embodiments of the invention include pharmaceutical compositions comprising one or more inhibitory peptides and a pharmaceutically acceptable carrier such as a peptide stabilizing excipient or an agent that inhibits microbial growth. Optionally at least one of the amino acids in the inhibitory peptide(s) comprises a non-natural amino acid; and/or the inhibitory peptide is coupled to a heterologous peptide tag. Embodiments of the invention include a kit comprising one or more of these peptides packaged in a container. Embodiments of the invention include expression vector encoding one or more of these peptides. Another embodiment of the invention is a complex comprising transthyretin (SEQ ID NO: 1) and one or more of the peptides disclosed herein Another embodiment of the invention is a method of making one or more of the peptides disclosed herein, comprising synthesizing such peptides chemically or producing them recombinantly. Another embodiment of the invention is a method for reducing or inhibiting transthyretin (SEQ ID NO: 1) aggregation, comprising contacting transthyretin amyloid fibrils with an inhibitory peptide found in Table 1 in an amount sufficient to reduce or inhibit transthyretin aggregation. Optionally in such methods, at least one of the amino acids in the inhibitory peptide(s) comprises a non-natural amino acid; and/or the inhibitory peptide is coupled to a heterologous peptide tag. In certain embodiments of this method, the transthyretin amyloid fibrils are within an in vivo environment. Another embodiment of the invention is a method of modulating the size or rate of growth of a transthyretin amyloid fibril, comprising contacting the fibril with one or more peptide having the inhibitory sequences disclosed herein in an environment where the inhibitory peptide contacts residues 22 to 48 (strands B and C), residues 86 to 97 (strand F), or residues 113 to 124 (strand H) of transthyretin; such that the contacted transthyretin amyloid fibril exhibits a modulated size or rate of growth.

A related embodiment of the invention is a method for blocking or inhibiting (preventing, stopping) the aggregation of transthyretin (TTR; e.g. a monomer, small aggregate, oligomer, or fibril of TTR) and its cytotoxicity. The method comprises contacting the transthyretin with an effective amount of an inhibitory peptide or pharmaceutical composition of the invention. The TTR molecule can be in solution or in a culture or in a subject. The contacting of a TTR molecule (monomer, oligomer, small aggregate or fibril) with an inhibitory peptide blocks or inhibits TTR aggregation and/or cytotoxicity. In a further embodiment, a method of blocking or inhibiting amyloidosis of transthyretin (TTR) in a subject is provided. The method comprises administering to the subject a pharmaceutical composition comprising an inhibitory peptide and a pharmaceutically acceptable carrier, so that amyloidosis of TTR in the subject is blocked or inhibited. In one or more embodiments, the inhibitory peptide comprises an amino acid sequence from Table 1. Typically, the inhibitory peptide binds to a segment of transthyretin which is responsible for the aggregation, such as an B, C, F or H strand of TTR.

Yet another embodiment of the invention is a method of observing the presence or absence of transthyretin amyloid fibrils in a biological sample comprising combining a biological sample with a peptide that binds to residues 22 to 48 (strands B and C), residues 86 to 97 (strand F), or residues 113 to 124 (strand H) of transthyretin (SEQ ID NO: 1), allowing the peptide to bind to transthyretin amyloid fibrils that may be present in the biological sample; and then monitoring this combination for the presence of complexes formed between transthyretin amyloid fibrils and the inhibitory peptide; wherein the presence of said complexes show the presence of transthyretin amyloid fibrils in the biological sample. Optionally in this embodiment, the presence of complexes formed between transthyretin amyloid fibrils and the inhibitory peptide is monitored using a detectable label that is coupled to the inhibitory peptide (e.g. a heterologous peptide tag). In certain embodiments, at least one inhibitory peptide comprises an inhibitory peptide sequence shown in Table 1.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

Figure 1:
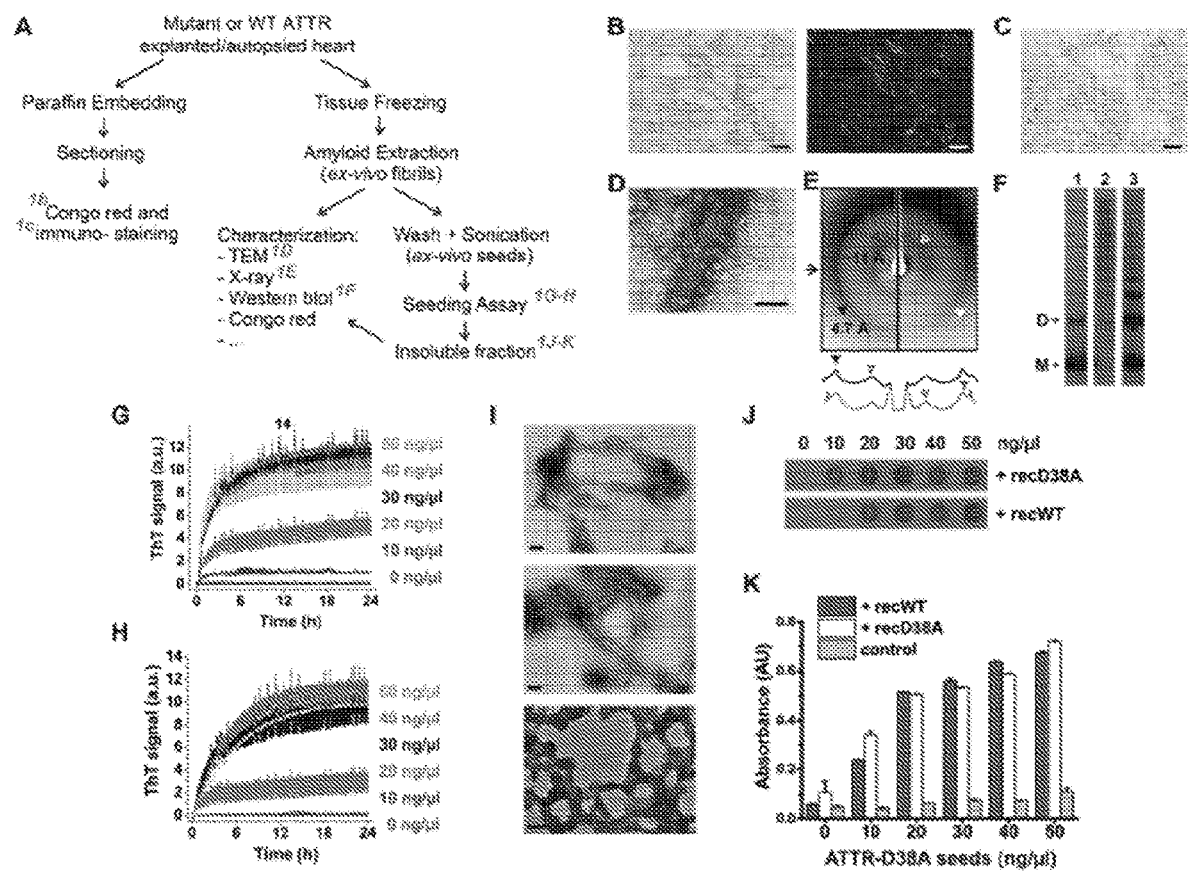
FIG. 1. Amyloid seeding by ex-vivo ATTR seeds extracted from the explanted heart of an ATTR-D38A patient. (A) Experimental outline with references to panels showing results. (B) Congo red staining of a cardiac section under bright field (left) and polarized light (right) showing strikes of apple-green birefringence. Scale bars, 50 µm. (C) Anti-TTR immuno-staining of a consecutive cardiac section. Scale bar, 100 µm. (D) Electron micrograph of ex-vivo fibrils. Scale bar, 100 nm. (E) X-ray diffraction of ex-vivo seeds (left, black arrowheads) and seeded fibrils (right, white arrowheads). Below, radial intensity profiles of diffraction patterns of seeds (black) and seeded fibrils (purple). Close and open arrowheads point to 4.7 Å and ~11 Å reflections, respectively. (F) Anti-TTR western blot of recombinant wild type transthyretin (lane 1, 0.3 µg), ex-vivo material (lane 2, 0.5 µg), and seeded fibrils (lane 3, 0.3 µg). M, 14 kDa monomer. D, 28 kDa dimer. (G-H) Amyloid seeding assays, followed by ThT fluorescence. Increasing amounts of ex-vivo seeds were added to recombinant D38A (G) or wild type TTR (H). a.u., arbitrary units. n=3. Error bars, S.D. (I) Electron micrographs of non-seeded aggregates (bottom), and seeded fibrils from recombinant D38A (top) and wild type TTR (middle). Scale bar, 100 nm. (J) Anti-his-tag immuno-dot blot and (K) 280 nm absorbance of insoluble fractions collected from G and H. Control, ex-vivo seeds in the absence of recombinant protein. AU, absorbance units.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. All publications, patents, and patent applications cited herein are hereby incorporated by reference in their entirety for all purposes. In the description of the preferred embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention.

Amyloid diseases are characterized by the deposition of a particular protein into amyloid fibrils. Amyloid fibrils are robust fibrillar structures with the potential to seed subsequent fibril formation of the parental protein in a process known as amyloid seeding. Here we investigate amyloid seeding in a disease model of amyloidosis, and explore inhibition of seeding via peptide inhibitors as a therapeutic strategy.

Structured amyloid proteins require local or total unfolding to expose hidden amyloidogenic segments that trigger fibril formation (18-20). In ATTR, initial TTR amyloid fibrils grow by a well-documented pathway involving dissociation of the native TTR tetramer dissociation to monomers, which then undergo a conformational change and form fibrils (18). The resulting fibrils are constituents of the "seeds" that we investigate here. The structural stabilization of the native form of amyloid proteins has been explored as a therapeutic strategy for amyloid diseases, especially for ATTR (21-24). Kelly and coworkers sought small molecules that bind within the internal cavity of tetrameric TTR and stabilize the tetrameric state (23). They discovered the compound tafamidis that significantly stabilizes transthyretin in vitro (25), which has been approved in Europe, Japan, Argentina and Mexico for treatment of neuropathic cases of ATTR-V30M for early stage disease (26, 27). However, tafamidis has shown limited efficacy when administered at later stages, or for long term treatment, or for ameliorating progression of cardiac weakening (28-30).

Amyloid fibril formation can be driven by short adhesive protein segments (31). In previous work we found that two TTR segments are the principal drivers of fibril formation. These are the segments that form the F and H beta strands in the native structure. These strands become exposed to solvent upon TTR dissociation to monomers, enabling their stacking into the steric zipper spines of amyloid fibrils (32, 33). Based on the structures of the amyloid fibrils formed by these two segments, we have designed peptides that block fibril formation (see Table 1 below). These inhibitors are designed to cap the tips of TTR fibrils (32).

Here we find that ex-vivo amyloid fibrils extracted from ATTR patients strongly seed fibril formation of both wild type and mutant transthyretin. Moreover, we find that structural stabilization of the parental protein fails to halt the process. Instead, our peptide inhibitors block this seeding in vitro, and show efficacy in *Drosophila* models of hereditary ATTR. Our results provide evidence that the inhibition of amyloid seeding is a promising therapeutic strategy for ATTR. Based on the studies of crystal structures of amyloid-driving segments, it is believed that the process of fibril formation of amyloid proteins starts by the exposure of the same fibril-driving segment in several identical protein molecules, allowing them to stack into beta-sheets and the sheets to interdigitate, forming thus a steric zipper, the spine of many amyloid-like fibrils [14, 15, 16, 17]. Without being limited to a particular theory, it is hypothesized that after dissociation of the TTR tetramer, one or several segments of TTR drive protein aggregation by self-association and formation of steric zipper spines of amyloid fibrils. Several models of the TTR amyloid spine have been proposed [18, 19, 20, 21], but the aggregation prone segments of the protein remain uncertain. Kelly et al. found that the TTR tetramer must undergo dissociation to its constituent monomers in order to enable partial denaturation that leads to amyloidogenesis [3]. Illustrative experiments described in the Examples section below have investigated the features of the monomer that cause it to aggregate, and have further identified the aggregation-driving segments that influence the process. Moreover, the examples demonstrate the effectiveness of peptide inhibitors of amyloid fibril formation of TTR. This work shows the design and optimization of specific binding peptides that act as inhibitors of protein aggregation. Specific aspects of this work and embodiments of the invention are discussed in the following sections.

Using established protocols, we extracted insoluble materials from cardiac and adipose tissues of ATTR patients and have shown that they contain TTR in the amyloid state (FIG. 1). We find that these "seeds" catalyze rapid fibril formation of both wild type and several variant TTRs associated with familial diseases. This finding means that the seeds eliminate the slow initial lag phase that characterizes the kinetics of unseeded amyloid fibril formation (44). In the lag phase, amyloid proteins self-associate slowly to form nuclei, specifying the bonding pattern of the fibrils. Soluble protein molecules then add to these nuclei to form fibrils in the more rapid growth phase. In our assays, nuclei are provided by ex-vivo TTR fibrils, thereby explaining the short lag phase observed. In regards to polymerization in the elongation phase, our results suggest that TTR amyloid seeding is driven by the so-called primary nucleation, which occurs by addition of amyloidogenic units to the tips of fibrils (45), since TTR amyloid seeding significantly increases when more fibril tips are created by sonication. Although other extracted components may also contribute to fibril formation, our results indicate that TTR fibrils that are present in ex-vivo ATTR extracts are responsible for the observed amyloid seeding effect.

A challenge to full understanding of the seeding of TTR fibrils by patient tissues is the discovery by Westermark and colleagues of two distinct patterns of amyloid deposition in ATTR patients. In Type A amyloidosis, TTR depositions contain in addition to full length TTR, a 79-residue truncated C-terminal fragment of TTR; in Type B patients, TTR depositions contain only full-length TTR (4, 11). In our analyses of ATTR cardiac seeds, six of eight samples contained traceable amounts of fragmented TTR. We observed that, with the exception of one ATTR case, amyloid seeding capacity correlates with the presence of C-terminal fragments in the extract (FIG. 2B). Consistent with this, clinical observations indicate that fibrils present in the heart of Type A patients contain more wild type TTR than fibrils of Type B patients (10). In our exception case, fibrils were extracted from an ATTR-T60 Å patient with the clearest clinical manifestation of neuropathy among the patients included in this study. In our assays, neither patient gender nor age correlate with seeding capacity (FIG. 2C). However, our limited number of specimens does not permit definite conclusions.

The powerful seeding effect of disease-related TTR fibrils is consistent with key observations about ATTR pathogenesis. Of particular importance, our findings explain why the treatment of liver transplantation for ATTR is not always effective and sometimes results in cardiac deposition of wild type TTR (14-17, 28, 46, 47). Because TTR is largely biosynthesized in the liver, transplantation with a liver that secretes wild type TTR should replace most circulating mutant TTR with wild type. But if mutant amyloid seeds remain in other tissues, our experiments suggest that the seeds are able to convert the wild type TTR provided by the new liver also to amyloid fibrils, perpetuating disease. Some reports associate post-surgical cardiac deposition with Type A pathology, probably because of its increased seeding capacity (10, 35) (FIG. 2B). There are also cases of rapid amyloid deposition in recipients of so-called domino liver transplantations (48). In this procedure, explanted livers from patients with familial ATTR are implanted in patients with fatal hepatic disorders. Some previous reports propose age as a main contributor to secondary cardiac deposition in domino liver transplant (49, 50). The presence of seeds in the explanted livers has also been proposed to be a cause of disease transmission in domino liver transplant recipients (51, 52).

Our finding that ATTR amyloid material seeds fibril formation of wild type transthyretin (FIG. 3) illuminates other puzzling observations about ATTR pathogenesis. Although found to be more stable than mutant variants in vitro, wild type TTR deposits in both hereditary and wild type ATTR (6). Previous studies have found a correlation of more rapid ATTR pathogenesis to less stable mutant TTR variants (5). However, if the stability of TTR is the principal factor in the formation of amyloid fibrils, it is puzzling that TTR amyloid deposits in hereditary ATTR patients contain 30-50% of the more stable wild type protein (16, 46, 53). However, the presence of wild type TTR is expected as a result of seeding of wild type by disease-related seeds, as shown in FIG. 2A.

Extensive studies by others have established that compounds such as tafamidis and diflunisal bind within TTR and stabilize its tetrameric structure, diminishing its rate of dissociation and hence its conversion to amyloid fibrils (23, 24, 39). The data of FIGS. 3, A and B, confirm the stabilization of TTR by tafamidis and diflunisal. Indeed tafamidis has been prescribed for treatment of ATTR-V30M, and ameliorates disease progression when administered at disease stage I (26, 27, 54, 55). Diflunisal has shown positive neurological effects in ATTR patients at different stages (56, 57).

Despite the stabilization, our results show that disease-related seeds convert wild type TTR into amyloid fibrils in the presence of these compounds (FIGS. 3, C and D) at concentrations that fully inhibit aggregation of recombinant transthyretin in the absence of seeds (25, 58). Thus our results offer an explanation for the reported limited efficacy of tafamidis over the long term, when administered at late stages, or on cardiac amyloid (28-30). That is, stabilization of tetrameric TTR may be insufficient in situations in which seeded polymerization operates rather than de-novo nucleation of TTR seeds.

Figure 3:
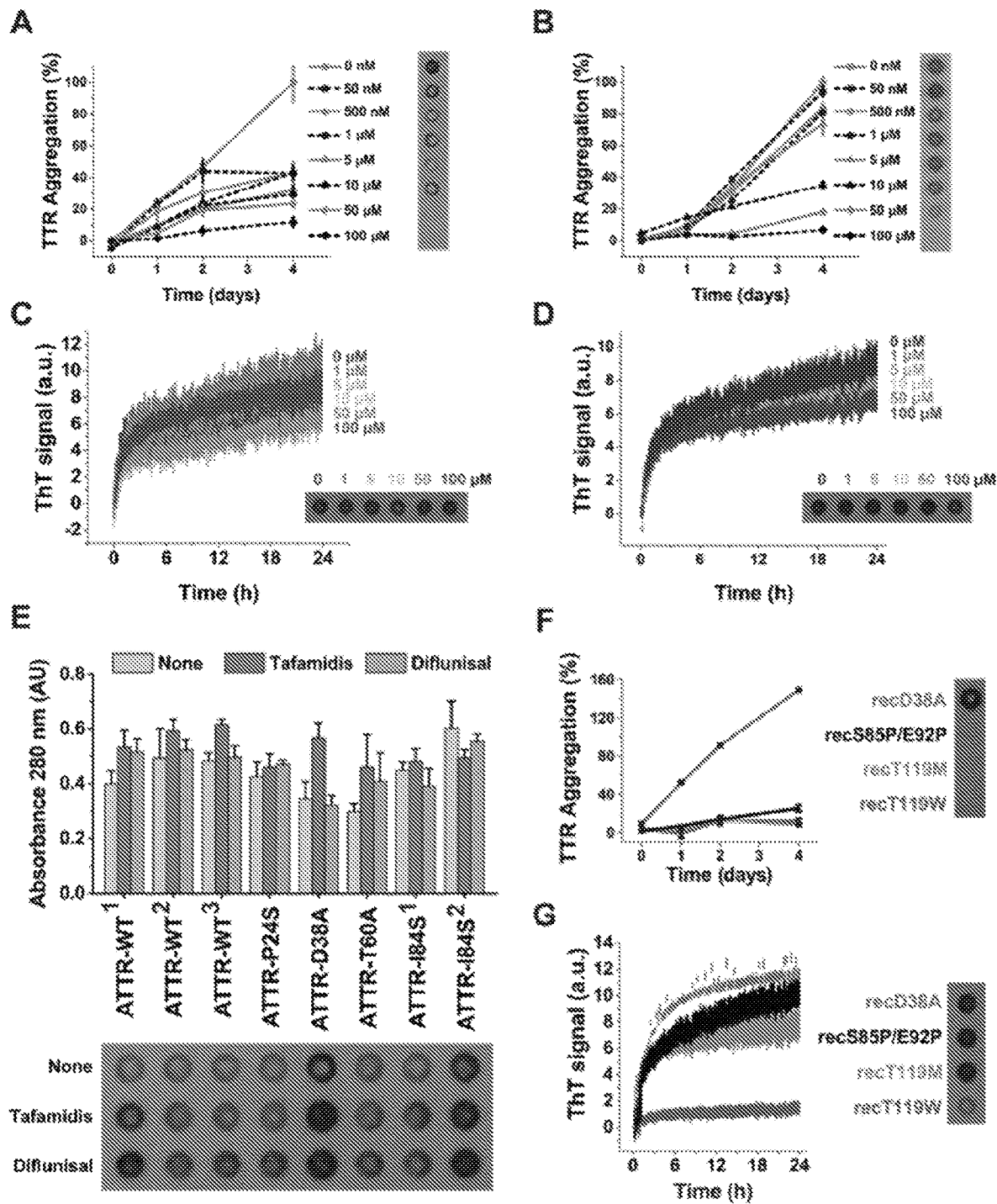
FIG. 3. Effect of tetramer stability on amyloid seeding. (A, B) TTR aggregation in the absence of seeds measured by absorbance at 400 nm. Increasing amounts of tafamidis (A) or diflunisal (B) as labeled were added to 1 mg/ml recombinant wild type TTR and the sample was incubated for 4 days. Absorbance measured after 4 days of incubation in the absence of compound was considered 100% aggregation because no soluble TTR was detected. Right insets, anti-TTR dot blot of insoluble fractions. (C, D) Amyloid seeding assay, followed by ThT fluorescence. Increasing amounts of tafamidis (C) or diflunisal (D) as labeled were added to 0.5 mg/ml recombinant wild type TTR and 30 ng/μl ATTR-D38A seeds. Insets, anti-TTR dot blot of insoluble fractions. n=3. Error bars, S.D. a.u., arbitrary units. (E) Amyloid seeding assay of 30 ng/μl ex-vivo seeds incubated with 0.5 mg/ml recombinant wild type transthyretin in the absence or presence of 180 μM tafamidis or 180 μM diflunisal. After 24 hours of incubation, the insoluble fraction was collected, and absorbance was measured. Bottom inset, anti-TTR dot blot of insoluble fractions. AU, absorbance units. (F) Aggregation assay of 1 mg/ml non-aggregating TTR mutants in the absence of seeds followed by absorbance. Aggregation of wild type transthyretin was considered as 100%. Right inset, anti-TTR dot blot of insoluble fractions. (G) Amyloid seeding assay of non-aggregating mutants in the presence of 30 ng/μl ATTR-D38A seeds, followed by ThT fluorescence. n=3. Error bars, S.D. a.u. arbitrary units. Right inset, anti-TTR dot blot of insoluble fractions.

The limited effect of TTR tetramer stabilizers in our experiments does not contradict the well established mechanism of de novo formation of TTR amyloid. Our experiments indicate that the conversion of TTR to amyloid fibrils requires the dissociation of tetramers and partial unfolding of monomers. These events trigger the well established downhill polymerization pathway, established by Kelly and colleagues (59). In our assays, amyloid seeding is performed at low pH to weaken the quaternary structure and to lead to tetramer dissociation. Under these conditions, the addition of seeds to recombinant TTR causes acceleration of fibril formation in a seeded polymerization pathway. In the patient, TTR dissociation may be affected by a variety of factors such as age, gender, pathology or genotype. Increased instability of mutated TTR, for instance, has been proposed to determine disease onset (5). We suggest that amyloid seeding may become pathologically relevant with advancing disease, after amyloid nuclei are formed from dissociated TTR The genetic variant T119M of TTR and its capacity to delay fibril formation was originally found in a ATTR-V30M family because of its protective effects; this variant remains soluble at pH 4.4 for weeks, if not months (32, 40, 60). However, in our experiments this stabilized variant does not halt conversion to amyloid in the presence of the disease-related seeds (FIGS. 3, F and G). These findings may explain why heterozygous individuals carrying both a familial amyloidogenic mutation, such as V30M, and the stabilizing T119M allele in time develop ATTR (40). In ATTR-V30M/T119M patients, we hypothesize that the mutation T119M may delay the progression of ATTR by reducing formation of seeds.

Figure 4:
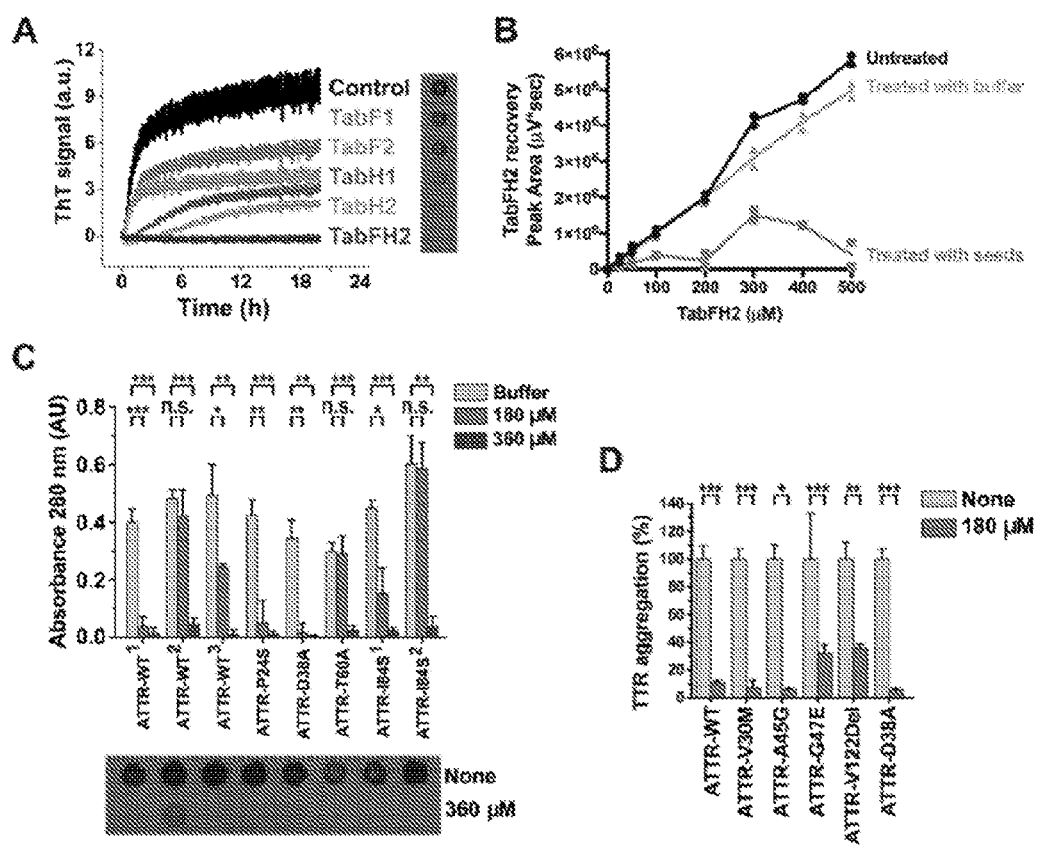
FIG. 4. Inhibition of amyloid seeding by designed inhibitors. (A) ThT assay to evaluate inhibition of seeding of ex-vivo ATTR-D38A by 180 μM designed inhibitors of TTR aggregation when added to 0.5 mg/ml recombinant wild type TTR. n=3. Error bars, S.D. Right inset, anti-TTR dot blot of insoluble fractions. (B) HPLC analysis of TabFH2 binding to ATTR-D38A seeds. ATTR-D38A seeds were immobilized on anti-TTR pre-coated well plates. Control wells were similarly treated with buffer. Increasing amounts of TabFH2 were added to independent wells pretreated with ATTR seeds (treated with seeds) or buffer (treated with buffer). After an incubation of 2 hours at room temperature, samples were collected and unbound TabFH2 was detected by HPLC. TabFH2 samples before treatment were included in the analysis (untreated). (C) Amyloid seeding inhibition by designed peptide inhibitors measured by absorbance of insoluble fractions collected after 24 h incubation of wild type TTR and 30 ng/μl ex vivo seeds extracted from the hearts of eight ATTR patients. n=3. Error bars, S.D. n.s., non-significant. $*p \leq 0.05$. $p \leq 0.005$, $*p \leq 0.0005$. AU, absorbance units. Bottom islet, anti-TTR dot blot of insoluble fractions. (D) Amyloid seeding of ex vivo seeds extracted from adipose biopsies in the presence of TabFH2. Buffer or 180 μM TabFH2 was added to 0.5 mg/ml recombinant wild type TTR and incubated with 10 ng/μl ex-vivo seeds for 24 hours. Amyloid seeding was visualized and quantified on a Celigo S Image system. Total aggregation was normalized to the absence of inhibitor. ATTR-D38A ex-vivo sample under the same conditions was included as a control. n=3. Error bars, S.D. n.s., non-significant. $*p \leq 0.05$. $p \leq 0.005$, $*p \leq 0.0005$.
Figure 5:
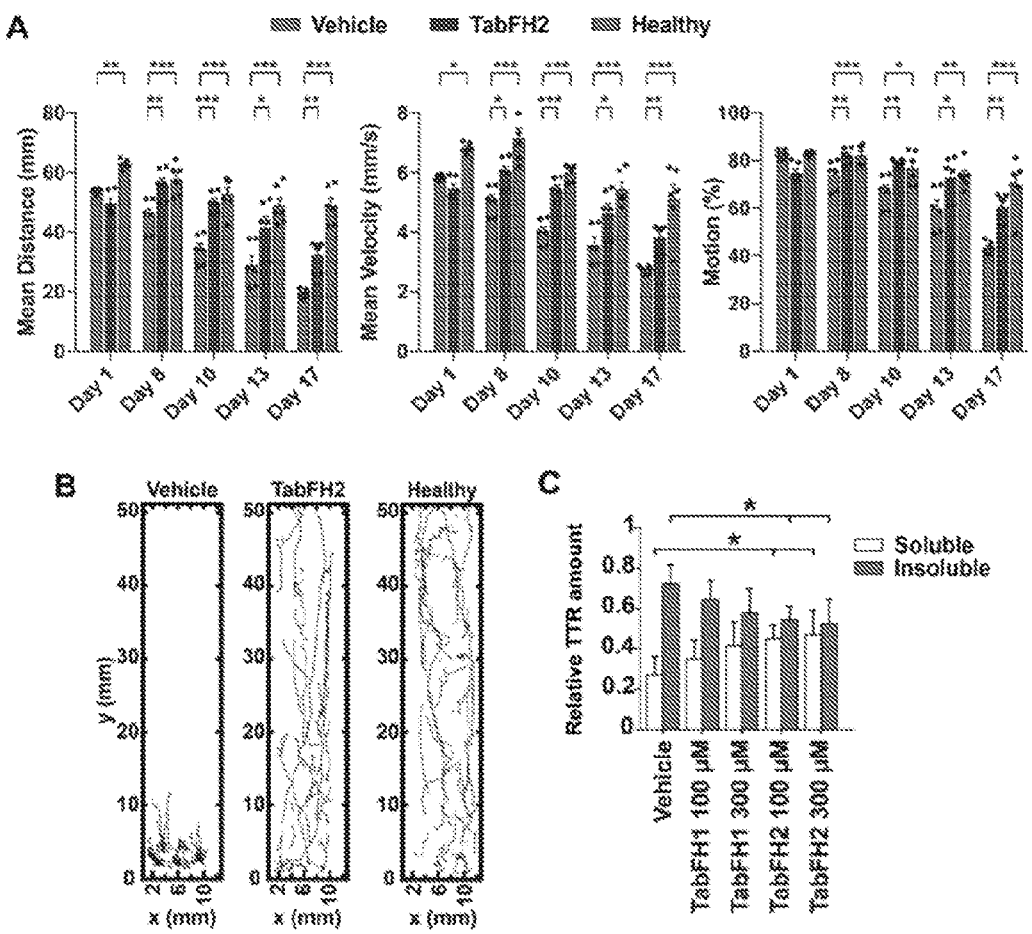
FIG. 5. Effects of TabFH2 on a disease model of *Drosophila melanogaster*. (A) Quantification of three motor parameters of TTR-A flies in climbing assays over time. Mean distance corresponds to mean length of trajectory of one fly in a vial. Mean velocity corresponds to the speed of 10 flies moving in one vial. Motion represents percentage of flies being in movement in one vial. A fly is considered in movement when its velocity is equal or higher than 2.5 mm/s. Flies were treated with vehicle or TabFH2 dissolved in food at 300 μM. Oregon flies were included as a healthy control. Dots represent single means computed from 6 independent measurements. Bars show mean values for those replicates. Error bars, S.E.M. $*p \leq 0.05$. $p \leq 0.005$. $*p \leq 0.0005$. (B) Two-dimensional drawing of 10 second trajectory traces recorded from Oregon flies (labeled as healthy), and TTR-A flies after 7 days of treatment with vehicle or TabFH2 at 300 μM. (C) Quantification of soluble and insoluble TTR in head homogenates obtained from TTR-A flies after 17 days of treatment with vehicle, TabFH1 or TabFH2. The soluble and insoluble fractions were obtained by homogenization with Triton and sequential centrifugation. 20 flies were used per condition. Protein fractions were equally loaded and separated by electrophoresis. TTR was detected by western blot using an anti-TTR polyclonal antibody. The quantification was performed on LabImage. Total amount of TTR per condition was used to normalize. n=4. Error bars, S.D.

The capping of TTR amyloid fibrils by designed peptides is an alternative approach to inhibit TTR fibril formation. Our results show that in cases for which stabilization of tetrameric TTR may not be fully effective in halting fibril formation (FIG. 3), capping of TTR fibrils by designed blockers of fibril elongation is effective (FIG. 4). This is of special importance for cardiac ATTR patients, who are often diagnosed when manifesting advanced TTR deposition and have limited access to treatment options. In the conditions of our experiments, TabFH2 blockers are effective in halting fibril formation caused by wild type ATTR seeds and also by seeds of at least nine disease-related variants, extracted from both cardiac and adipose specimens. We find the inhibition of amyloid seeding by peptide inhibitors is an effective strategy independently of pathological variant, reaching full inhibition at a peptide concentration of 360 µM (FIG. 4C). TabFH2 blockers resulted in motor improvement and reduction of TTR deposition when administered to disease models of *Drosophila* (FIG. 5).

The general approach of capping for amyloid inhibition has previously been shown to be effective for blocking fibrils of other proteins: constructs of tau in vitro, and p53 in vitro and in mice (61, 62). In our previous work on inhibition of TTR, we used the steric zipper structures of β-strands F and H to design the TabFH1 peptide blockers (32). However, a limitation of the TabFH1 blockers is that they themselves form fibrils at high concentration. The TabFH2 inhibitors designed in the present study do not share this limitation and show improved efficiency.

The disclosure provided herein has two principal findings: (i) TTR amyloid aggregates extracted from tissues of ATTR patients powerfully accelerate the conversion of wild type and variant TTR into amyloid fibrils; and (ii) designed peptides that cap TTR amyloid fibrils can inhibit this process of seeding in vitro, and also in fly models of ATTR. The importance of seeding for conversion of soluble proteins to pathogenic amyloid fibrils was recognized by Robert Kisilevsky and colleagues beginning in the late 1970's (63-66). They described the so-called amyloid enhancing factor in a mouse model of AA amyloidosis, which they defined as a transferable activity that reduces the induction time of splenic deposition of the amyloid protein. Here we document the power of disease-related seeds of TTR amyloid to convert native tetrameric wild type TTR to amyloid, even when stabilized by drugs or by mutation. This finding helps to explain why disease symptoms persist in patients even after the main source of disease-prone TTR has been removed. Our results also provide evidence that the inhibition of elongation of TTR fibrils by designed inhibitors may be a plausible treatment for ATTR cases. We envision combinatory treatments for ATTR targeting protein expression, protein stability, deposit clearance and amyloid seeding (25, 57, 67-71).

We previously identified two segments of transthyretin that drive amyloid fibril formation (Strand F and Strand H), and designed specific peptide inhibitors that block TTR aggregation in vitro by capping fibril tips (listed in Table A below as FH1-mA and FH2-mE). These inhibitors contain non-natural amino acids (N-methyl groups) and exhibit a somewhat limited efficacy. As described herein, we have invented an optimized inhibitors for Strands F and H, TabFH2 (cocktail containing the inhibitors listed in Table A as FH2-mA and FH2-mE). They also contain non-natural amino acids with N-methyl groups to prevent fast degradation, and do not contain the wild-type sequence and shows improved effectiveness.

TABLE A

Structure-based designed inhibitors of TTR aggregation (N-me-E is N-methyl glutamate and N-me-A is N-methyl alanine)

| | |
|---|---|
| FH1-mE: RRRRPFHEHA(N-me-E)VVFTA | (SEQ ID NO: 70) |
| FH1-mA: RRRRPYSYSTT(N-me-A)VVTN | (SEQ ID NO: 71) |
| FH2-mE: RRRRHVAHPFV(N-me-E)FTE | (SEQ ID NO: 72) |
| FH2-mA: RRRRSYVTNPTSY(N-me-A)VT | (SEQ ID NO: 73) |

The inhibitor TabFH2 blocks fibril growth and halts amyloid seeding caused by TTR fibrils extracted from explanted tissues of 13 ATTR (TTR amyloidosis) patients. As described herein, we found that small amyloid seeds present in the tissues from ATTR patients have the capacity to cause rapid fibril formation of native transthyretin (TTR) (FIG. 1). This phenomenon is known as amyloid seeding.

Figure 2:
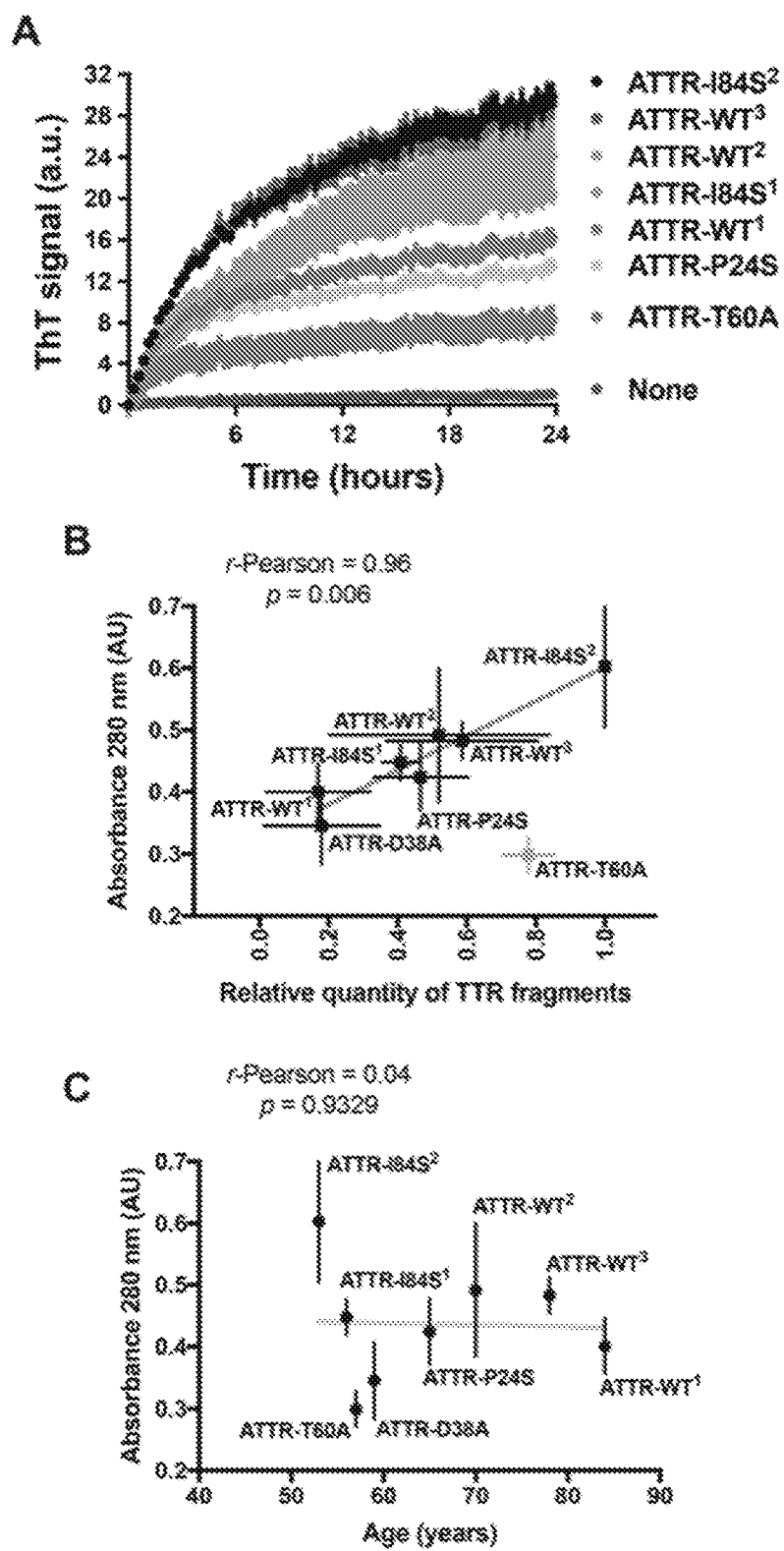
FIG. 2. Amyloid seeding by ATTR material extracted from the hearts of eight ATTR patients. (A) Amyloid seeding assay of wild type recombinant TTR in the presence of 30 ng/µl ATTR seeds extracted from the hearts of ATTR patients with various genetic backgrounds (as labeled), followed by Thioflavin T (ThT) fluorescence. Superscripts are used to differentiate ATTR patients with the same genetic background. n=3. Error bars, S.D. a.u., arbitrary units. (B) Comparison of amyloid seeding capacity (vertical axis) and relative quantity of truncated TTR of ex-vivo seeds. Truncated TTR content was quantified by ImageJ from two independent western-blots. (C) Comparison of amyloid seeding capacity of ex-vivo seeds (vertical axis) and ATTR patient age. There were only two specimens obtained from female patients: ATTR-D38A and ATTR-I84S[1]. In both B and C, amyloid seeding capacity was measured as follows: 30 ng/µl seeds were incubated with 0.5 mg/ml recombinant wild type TTR and 280 nm absorbance of the insoluble fraction collected after seeding for 24 hours was measured, and lineal regression and Pearson r were obtained by Origin-Lab.

We are the first to discover this pathological phenomenon and there are no current therapeutic efforts that target it. One medical important implication is that the present treatment for ATTR is liver transplantation, because the new liver produces only wild type TTR, which is expected not to form fibrils. But we show here that the TTR amyloid seeds in the explanted patient tissues DO seed wild type TTR. This explains why many ATTR patients who receive liver transplants continue to decline and die. Our new inhibitors TabFH2 block this seeding, and hence can be used as a therapy to stop seeding and halt ATTR disease (FIG. 3). In addition, unlike our inhibitors, TTR stabilizers such as tafamidis (sold by Pfizer) and diflunisal do not halt TTR amyloid seeding. We found that the addition of tafamidis and diflunisal do not reduce amyloid seeding capacity of any of the human tissue samples that we have investigated (FIG. 2).

The only treatment approved in the US for hereditary cases of ATTR is liver transplantation (because the new liver secretes wildtype, rather than mutant, TTR). Although this procedure replaces the majority of circulating TTR mutant for the wild-type variant, it is often followed by cardiac deposition and heart failure. The alternative treatment Tafamidis, approved in Europe but not in the US, has shown no significant effect at late stages of the disease. Our results indicate that TTR seeds present in ATTR patients have the capacity to cause rapid fibril formation of wild-type transthyretin, even when stabilized by tafamidis or other protein stabilizers. Additional strategies are required to halt amyloid seeding in these patients, such as our inhibitor TabFH2. Note: TabFH2 refers to the two inhibitors that block fibril formation of Strands F and H.

The invention disclosed herein has a number of embodiments. One embodiment is a composition of matter comprising at least one inhibitory peptide and transthyretin (TTR) or a segment of TTR which is responsible for the aggregation of TTR, such as an B, C, F or H strand of TTR. A pharmaceutically acceptable carrier selected to be compatible with the inhibitory peptide may also be included. In embodiments of the invention the inhibitory peptide can include one or more non-naturally occurring amino acids and/or can be coupled to a heterologous peptide tag. The heterologous peptide tag can comprise an amino acid sequence that increases peptide solubility (e.g. a plurality of arginine residues); and/or an amino acid sequence that facilitates monitoring or manipulation of the peptide (e.g. a plurality of lysine or histidine residues). In one or more embodiments, the inhibitory peptide comprises an amino acid sequence from Table 1 (optionally with a heterologous peptide tag such as "RRRR" (SEQ ID NO: 69) as shown in this Table):

TABLE 1

ARGININE SUBSTITUTION SCREENING

| Peptide # | Sequence | A. Overall Rosetta energy (kcal/mol) |
|---|---|---|
| Strand F | | |
| 1 (SEQ ID NO: 9) | RRRRPRHEHAEVVFTA | −123.9 |
| 2 (SEQ ID NO: 10) | RRRRPFREHAEVVFTA | −118.3 |
| 3 (SEQ ID NO: 11) | RRRRPFHRHAEVVFTA | −117.1 |
| 4 (SEQ ID NO: 12) | RRRRPFHERAEVVFTA | −115.8 |
| 5 (SEQ ID NO: 13) | RRRRPFHEHREVVFTA | −107.2 |
| 6 (SEQ ID NO: 14) | RRRRPFHEHARVVFTA | −105.6 |
| 7 (SEQ ID NO: 15) | RRRRPFHEHAERVFTA | −97.6 |
| 8 (SEQ ID NO: 16) | RRRRPFHEHAEVRFTA | −93.5 |
| 9 (SEQ ID NO: 17) | RRRRPFHEHAEVVRTA | −113.8 |
| 10 (SEQ ID NO: 18) | RRRRPFHEHAEVVFRA | −118.1 |
| TabF1 (SEQ ID NO: 19) | RRRRPFHEHAEVVETA | −125.3 |
| Strand H | | |
| 1 (SEQ ID NO: 20) | RRRRPRSYSTTAVVTN | −125.9 |
| 2 (SEQ ID NO: 21) | RRRRPYRYSTTAVVTN | −121.5 |
| 3 (SEQ ID NO: 22) | RRRRPYSRSTTAVVTN | −118.7 |
| 4 (SEQ ID NO: 23) | RRRRPYSYRTTAVVTN | −106.8 |
| 5 (SEQ ID NO: 24) | RRRRPYSYSRTAVVTN | −118.9 |
| 6 (SEQ ID NO: 25) | RRRRPYSYSTRAVVTN | −111.1 |
| 7 (SEQ ID NO: 26) | RRRRPYSYSTTRVVTN | −109.2 |
| 8 (SEQ ID NO: 27) | RRRRPYSYSTTARVTN | −104.2 |
| 9 (SEQ ID NO: 28) | RRRRPYSYSTTAVRTN | −111.1 |
| 10 (SEQ ID NO: 29) | RRRRPYSYSTTAVVRN | −119.7 |
| TabH1 (SEQ ID NO: 30) | RRRRPYSYSTTAVVTN | −128.1 |

TABLE 1

SWAPPING SCREENING

| Peptide # | Sequence | A. Overall Rosetta energy (kcal/mol) | B. ThT signal (20h, no inhibitor was normalized to 100%, SD = 11.42) |
|---|---|---|---|
| Strand F | | | |
| F1 (SEQ ID NO: 31) | RRRRVEHAVEAHFTFP | −175.6 | |
| F2 (SEQ ID NO: 32) | RRRRAFEAHVHTEFVP | −172.4 | |
| F3 (SEQ ID NO: 33) | RRRREHHFFEAVVATP | −169.3 | |
| F4 (SEQ ID NO: 34) | RRRREHVAHFFVETPA | −155.7 | |
| F5 (SEQ ID NO: 35) | RRRREHVFVHEFATPA | −152.9 | |
| F6 (SEQ ID NO: 36) | RRRRPEFEVAAVFHTH | −130.8 | |
| F7 (SEQ ID NO: 37) | RRRRPFAAVFHVEEHT | −130.6 | |
| F8 (SEQ ID NO: 38) | RRRRHAEVFVEHAPTF | −129.1 | |
| F9 (SEQ ID NO: 39) | RRRRHHAFAVFEVPTE | −127.7 | |
| TabF1 (SEQ ID NO: 40) | RRRRPFHEHAEVVFTA | −125.3 | 60.45 ± 3.90 (N-me-A12) |
| F10 (SEQ ID NO: 41) | RRRRFVHVTAFEPAHE | −110.9 | |
| F11 (SEQ ID NO: 42) | RRRREHAHVFAVPTFE | −110.7 | |
| F12 (SEQ ID NO: 43) | RRRRPAVTAFEHVEH | −104.5 | |

TABLE 1-continued

SWAPPING SCREENING

| Peptide # | Sequence | A. Overall Rosetta energy (kcal/mol) | B. ThT signal (20h, no inhibitor was normalized to 100%, SD = 11.42) |
|---|---|---|---|
| F13 (SEQ ID NO: 44) | RRRREVPHVAHAEFFT | -92.4 | |
| F14 (SEQ ID NO: 45) | RRRREFTVEAFPHAHV | -87.8 | |
| F15 (SEQ ID NO: 46) | RRRRHVAHPFVEFTEA | -64.1 | |
| TabF2 (SEQ ID NO: 47) | RRRRHVAHPFVEFTE | -43.8 | 40.48 ± 4.68 (N-me-E12) |
| F16 (SEQ ID NO: 48) | RRRRHFEAFPEHVVAT | -61.2 | 116.35 ± 6.38 (N-me-E11) |
| F17 (SEQ ID NO: 49) | RRRRHFEVAFPVEHAT | -58.3 | 62.84 ± 7.05 (N-me-E13) |
| Strand H | | | |
| H1 (used as negative control) (SEQ ID NO: 50) | RRRRNVTTSYYTVASP | -170.4 | 120.50 ± 14.26 (N-me-A14) |
| H2 (SEQ ID NO: 51) | RRRRAVSVSYTYTNPT | -166.2 | |
| H3 (SEQ ID NO: 52) | RRRRNTAYSVVTSTPY | -162.5 | |
| H4 (SEQ ID NO: 53) | RRRRTTAYSTNVSYPV | -147.8 | |
| H5 (SEQ ID NO: 54) | RRRRPATYNSTSVVTY | -141.7 | |
| H6 (SEQ ID NO: 55) | RRRRTNVYYSTAVPTS | -136.7 | |
| H7 (SEQ ID NO: 56) | RRRRPYAVNYTSTSTV | -135.6 | |
| H8 (SEQ ID NO: 57) | RRRRTYANTVYSTPVS | -133.7 | |
| TabH1 (SEQ ID NO: 58) | RRRRPYSYSTTAVVTN | -128.1 | 32.48 ± 2.39 (N-me-E11) |
| H9 (SEQ ID NO: 59) | RRRRSASTYYVTPNVT | -116.2 | |
| H10 (SEQ ID NO: 60) | RRRRYVPTTVAYNSST | -87.1 | |
| H11 (SEQ ID NO: 61) | RRRRVTSPTAVSYTYN | -77.8 | |
| H12 (SEQ ID NO: 62) | RRRRTSYPNSVTTAYV | -76.7 | |
| H13 (SEQ ID NO: 63) | RRRRSYYVPVSTTNTA | -70.9 | |
| H14 (SEQ ID NO: 64) | RRRRYVSNPTSTYVAT | -69.0 | 64.43 ± 4.71 (N-me-A14) |
| TabH2 (SEQ ID NO: 65) | RRRRSYVTNPTSYAVT | -66.4 | 22.40 ± 1.09 (N-me-E12) |
| H15 (SEQ ID NO: 66) | RRRRVANTSPTSYYVT | -63.3 | 48.29 ± 5.53 (N-me-A6) |

The inhibitory peptide may be synthesized (e.g., chemically or by recombinant expression in a suitable host cell) by any of a variety of art-recognized methods. Certain aspects of the invention include a polynucleotide encoding the inhibitory peptide; an expression vector comprising the polynucleotide; a cell transfected with the polynucleotide or the expression vector; and a method of making the peptide, comprising expressing it in the transfected cell, cultivating the cell and harvesting the peptide thus generated.

Another aspect of the invention is a kit comprising an inhibitory peptide of the invention, optionally packaged in a container. The kit may comprise a suitable amount of an inhibitory peptide of the invention; reagents for generating the peptide; reagents for assays to measure their functions or activities; or the like. Kits of the invention may comprise instructions for performing a method. Other optional elements of a kit of the invention include suitable buffers, media components, or the like; a computer or computer-readable medium providing the structural representation of the crystal structure described herein; containers; or packaging materials. Reagents for performing suitable controls may also be included. The reagents of the kit may be in containers in which the reagents are stable, e.g., in lyophilized form or stabilized liquids. The reagents may also be in single use form, e.g., in single reaction form for administering to a subject. A further aspect is a kit for carrying out any of the methods described herein.

Another embodiment is a method for blocking or inhibiting (preventing, stopping) the aggregation of transthyretin (TTR; e.g. a monomer, small aggregate, oligomer, or fibril of TTR) and/or TTR cytotoxicity. The method comprises contacting the transthyretin with an effective amount of an inhibitory peptide or pharmaceutical composition of the invention. The contacting of a TTR molecule (monomer, oligomer, small aggregate or fibril) with an inhibitory peptide blocks or inhibits TTR aggregation and/or cytotoxicity. In one or more embodiments, the inhibitory peptide comprises an amino acid sequence from Table 1. In specific instances, the inhibitory peptide consists of an amino acid sequence from Table 1. The inhibitory peptide and the TTR may be bound to, conjugated with, or otherwise associated with each other. Typically, the inhibitory peptide binds to a segment of transthyretin which is responsible for the aggregation, such as an F or H strand of TTR. The inhibitory peptide and the TTR may be covalently or non-covalently linked. The TTR can be in solution or in a cell, which is in culture or in a subject.

Generally, the peptide inhibitors of the inventor bind specifically to TTR. For example, the binding can be 2, 5, 10 or 100 times stronger or no binding at all can be detected for an unintended target. Conventional methods can be used to determine the specificity of binding, e.g. competitive binding assays or other suitable analytic methods.

An "effective amount" of a compound or a pharmaceutical composition is an amount that can elicit a measurable amount of a desired outcome, e.g. inhibition of TTR aggregation or cytotoxicity; for a diagnostic assay, an amount that can detect a target of interest, such as a TTR aggregate; or in a method of treatment, an amount that can reduce or ameliorate, by a measurable amount, a symptom of the disease or condition that is being treated.

In a further embodiment, a method of blocking or inhibiting amyloidosis of transthyretin (TTR) in a subject is provided. The method comprises administering to the subject a pharmaceutical composition comprising an inhibitory peptide binds to TTR or a segment of TTR which is responsible for the aggregation of TTR, such as an F or H strand of TTR. In one or more embodiments, the pharmaceutical composition comprises an inhibitory peptide comprising an amino acid sequence from Table 1 and a pharmaceutically acceptable carrier, so that amyloidosis of TTR in the subject is blocked or inhibited. In specific instances, the inhibitory peptide consists of an amino acid sequence from Table 1. The pharmaceutical composition may be administered to a subject having a disease or condition associated with amyloidosis of TTR (e.g. wild-type amyloidosis, hereditary amyloidosis).

Yet another embodiment of the invention is a method of observing the presence or absence of transthyretin amyloid fibrils in a biological sample comprising combining a biological sample with a peptide that binds to residues 22 to 48 (strands B and C), residues 86 to 97 (strand F), or residues 113 to 124 (strand H) of transthyretin (SEQ ID NO: 1), allowing the peptide to bind to transthyretin amyloid fibrils that may be present in the biological sample; and then monitoring this combination for the presence of complexes formed between transthyretin amyloid fibrils and the inhibitory peptide; wherein the presence of said complexes show the presence of transthyretin amyloid fibrils in the biological sample. Optionally in this embodiment, the presence of complexes formed between transthyretin amyloid fibrils and the inhibitory peptide is monitored using a detectable label that is coupled to the inhibitory peptide (e.g. a heterologous peptide tag). In certain embodiments, at least one inhibitory peptide comprises an inhibitory peptide sequence shown in Table 1. Optionally, the method is performed on a biological sample obtained from an individual suspected of suffering from wild-type or hereditary TTR amyloidosis.

While it is possible for the inhibitory peptide (i.e. active ingredient) of the composition to be administered without other ingredients, it is often preferable to present them within a pharmaceutical formulation. Pharmaceutical formulations according to the present invention comprise the inhibitory peptide together with one or more pharmaceutically acceptable carriers or excipients and optionally other therapeutic agents. The carrier(s) must be acceptable in the sense of being compatible with the other ingredients of the formula. In embodiments of the invention, the composition comprises a pharmaceutically acceptable carrier selected to be compatible with the inhibitory peptide. One or more accessory ingredients may also be included. Such accessory ingredients include those conventional in the art, such as, fillers, binders, diluents, disintegrants, lubricants, colorants, flavoring agents and wetting agents.

The inhibitory peptides described herein also include active variants or optimizations thereof. An "active variant" is a variant which retains at least one of the properties of the inhibitory peptides described herein (e.g. the ability to bind to TTR; the ability to block, inhibit or prevent TTR aggregation and/or TTR cytotoxicity). Amino acids may be added, removed or substituted from the specific inhibitory peptide sequences described herein to generate such variants. Suitable active variants also include peptidomimetic compounds (any compound containing non-peptidic structural elements that is capable of mimicking the biochemical and/or biological action(s) of a natural mimicked peptide, including, for example, those designed to mimic the structure and/or binding activity peptides according to the methods disclosed herein).

In one embodiment, active variants of the inhibitory peptides are shortened by 1-3 (e.g., 1, 2 or 3) amino acids at either the N-terminus, the C-terminus, or both of the starting inhibitory peptide. In another embodiment, the active variants are lengthened (extended) by 1, 2, 3 or 4 amino acids at the C-terminal end of the starting inhibitory peptide, e.g. with amino acid residues at the position at which they occur in TTR.

A variety of other types of active variants are encompassed. In some embodiments, amino acids other than the ones noted above in the consensus sequence are substituted. These amino acids can help protect the peptide inhibitors against proteolysis or otherwise stabilize the peptides, and/or contribute to desirable pharmacodynamic properties in other ways. In some embodiments, the non-natural amino acids allow an inhibitor to bind more tightly to the target because the side chains optimize hydrogen bonding and/or apolar interactions with it. In addition, non-natural amino acids offer the opportunity of introducing detectable markers, such as strongly fluorescent markers which can be used, e.g., to measure values such as inhibition constants. Also included are peptide mimetics, such as, e.g., peptoids, beta amino acids, N-ethylated amino acids, and small molecule mimetics.

In one embodiment, non-natural amino acids are substituted for amino acids in the sequence. More than 100 non-natural amino acids are commercially available. These include, for example:

Non-Natural Amino Acids which can Substitute for LEU:

| | |
|---|---|
| Fmoc-L-cyclohexylglycine | 161321-36-4 |
| Fmoc-L-phenylglycine | 102410-65-1 |
| Fmoc-4-hydroxy-D-phenylglycine | 178119-93-2 |
| Fmoc-L-α-t-butylglycine | 132684-60-7 |
| Fmoc-cyclopentyl-Gly-OH | 220497-61-0 |
| Fmoc-L-2-indanylglycine | 205526-39-2 |

Non-Natural Amino Acids which can Substitute for THR:
Fmoc-Thr(tBu)-OH 71989-35
0
Fmoc—(RS)-2-amino-3-hydroxy-3-methylbutanoic acid 105504-72-1
Non-Natural Amino Acids which can Substitute for ILE:

| | |
|---|---|
| Fmoc-allo-Ile-OH | 251316-98-0 |
| Boc-N-Me-allo-Ile-OH | 136092-80-3 |
| Fmoc-Homoleu-OH | 180414-94-2 |

Non-Natural Amino Acids which can Substitute for ARG:

| | |
|---|---|
| Fmoc-Nω-nitro-L-arginine | 58111-94-7 |
| Fmoc-L-citrulline | 133174-15-9 |

Non-Natural Amino Acids which can Substitute for TYR:

| | |
|---|---|
| Fmoc-3-amino-L-tyrosine | 726181-70-0 |
| Fmoc-3-nitro-L-tyrosine | 136590-09-5 |
| Fmoc-3-methoxy-L-tyrosine | |
| Fmoc-3-iodo-L-tyrosine | 134486-00-3 |
| Fmoc-3-chloro-L-tyrosine | 478183-58-3 |
| Fmoc-3,5-dibrimo-L-tyrosine | 201484-26-6 |

Non-Natural Amino Acids which can Substitute for LYS:

| | |
|---|---|
| Fmoc-Lys(retro-Abz-Boc)-OH | 159322-59-5 |
| Fmoc-Lys(Mca)-OH | 386213-32-7 |
| Fmoc-(Nδ-4-methyltrityl)-L-ornithine | 343770-23-0 |
| N-α-Fmoc-N-ε-(d-Biotin)-L-lysine | 146987-10-2 |

In another embodiment, one or more (e.g. 1, 2, 3, 4, 5, 6, 7, 8, 9, 10, 11, 12, 13, 14, 15, 16 or 17)N-methylated residues are included in the peptide.

An inhibitory peptide of the invention can comprise, e.g., L-amino acids, D-amino acids, non-natural amino acids, or combinations thereof.

Active variants include molecules comprising various tags at the N-terminus or the C-terminus of the peptide. For example, a peptide having the sequence of SEQ ID No. 1-4 can comprise as tags as its N-terminus and/or at its C-terminus: 1, 2, 3, 4, 5, 6, 7, 8, 9 or 10 Lysine residues; 1, 2, 3, 4, 5, 6, 7, 8, 9 or 10 Arginine residues; 1, 2, 3, 4, 5, 6, 7, 8, 9 or 10 Glutamate residues; 1, 2, 3, 4, 5, 6, 7, 8, 9 or 10 Aspartate residues; combinations of these amino acid residues; or other polar tags that will be evident to a skilled worker. Other active variants include mutations of the sequences of the inhibitory peptide sequence which increase affinity of the inhibitory peptides for the TTR molecule (oligomer, fibril, etc.).

In one embodiment of the invention, an inhibitory peptide of the invention is isolated or purified, using conventional techniques such as the methods described herein. By "isolated" is meant separated from components with which it is normally associated, e.g., components present after the peptide is synthesized. An isolated peptide can be a cleavage product of a protein which contains the peptide sequence. A "purified" inhibitory peptide can be, e.g., greater than 90%, 95%, 98% or 99% pure.

In embodiments of the invention, the inhibitory peptide is detectably labeled. Labeled peptides can be used, e.g., to better understand the mechanism of action and/or the cellular location of the inhibitory peptide. Suitable labels which enable detection (e.g., provide a detectable signal, or can be detected) are conventional and well-known to those of skill in the art. Suitable detectable labels include, e.g., radioactive active agents, fluorescent labels, and the like. Methods for attaching such labels to a protein, or assays for detecting their presence and/or amount, are conventional and well-known.

An inhibitory peptide of the invention can be synthesized (e.g., chemically or by recombinant expression in a suitable host cell) by any of a variety of art-recognized methods. In order to generate sufficient quantities of an inhibitory peptide for use in a method of the invention, a practitioner can, for example, using conventional techniques, generate nucleic acid (e.g., DNA) encoding the peptide and insert it into an expression vector, in which the sequence is under the control of an expression control sequence such as a promoter or an enhancer, which can then direct the synthesis of the peptide. For example, one can (a) synthesize the DNA de novo, with suitable linkers at the ends to clone it into the vector; (b) clone the entire DNA sequence into the vector; or (c) starting with overlapping oligonucleotides, join them by conventional PCR-based gene synthesis methods and insert the resulting DNA into the vector. Suitable expression vectors (e.g., plasmid vectors, viral, including phage, vectors, artificial vectors, yeast vectors, eukaryotic vectors, etc.) will be evident to skilled workers, as will methods for making the vectors, inserting sequences of interest, expressing the proteins encoded by the nucleic acid, and isolating or purifying the expressed proteins.

Another aspect of the invention is a pharmaceutical composition comprising one or more of the inhibitory peptides and a pharmaceutically acceptable carrier. The components of the pharmaceutical composition may be detectably labeled, e.g. with a radioactive or fluorescent label, or with a label that is suitable for detection by positron emission spectroscopy (PET). In some embodiments, the inhibitory peptide is present in an effective amount for the desired purpose.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use. For example, "pharmaceutically acceptable salts" of a compound means salts that are pharmaceutically acceptable, as defined herein, and that possess the desired pharmacological activity of the parent compound.

Other aspects of the invention include: a polynucleotide encoding an inhibitory peptide of the invention. In embodiments of the invention, the polynucleotide is operably linked to a regulatory control sequence (e.g., a promoter or an enhancer) to facilitate production of the encoded protein following introduction (e.g. by transfection) into a suitable cell; a cell comprising the expression vector; and a method of making an inhibitory peptide of the invention comprising cultivating the cell and harvesting the peptide thus generated.

As used throughout this application, "about" means plus or minus 5% of a value.

Characterization of candidate inhibitory peptides of the invention can be carried out by any of a variety of conventional methods. For example, the peptides can be assayed for the ability to reduce or inhibit TTR aggregation or cytotoxicity. The assays can be carried out in vitro or in vivo. Suitable assays will be evident to a skilled worker; some suitable assays are described herein.

One aspect of the invention is a method for reducing or inhibiting TTR aggregation, comprising contacting TTR amyloid protofilaments with an effective amount of one or more of the inhibitory peptides of the invention. Such a method can be carried out (in solution) or in a cell (e.g. cells in culture or in a subject).

Another aspect of the invention is a method for treating a subject having a disease or condition which is mediated by the presence of fibrillated TTR (sometimes referred to herein as an TTR-mediated disease or condition). Among such diseases or conditions are, e.g., hereditary amyloidosis and wild-type TTR amyloidosis.

A "subject" can be any subject (patient) having aggregated (fibrillated) TTR molecules associated with a condition or disease which can be treated by a method of the present invention. In one embodiment of the invention, the subject has TTR amyloidosis. Typical subjects include vertebrates, such as mammals, including laboratory animals, dogs, cats, non-human primates and humans.

The inhibitors of the invention can be formulated as pharmaceutical compositions in a variety of forms adapted to the chosen route of administration, for example, orally, nasally, intraperitoneally, or parenterally, by intravenous, intramuscular, topical or subcutaneous routes, or by injection into tissue.

Suitable oral forms for administering the compounds include lozenges, troches, tablets, capsules, effervescent tablets, orally disintegrating tablets, floating tablets designed to increase gastric retention times, buccal patches, and sublingual tablets.

The compounds of the invention may be systemically administered, e.g., orally, in combination with a pharmaceutically acceptable vehicle such as an inert diluent or an assimilable edible carrier, or by inhalation or insufflation. They may be enclosed in coated or uncoated hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. For compositions suitable for administration to humans, the term "excipient" is meant to include, but is not limited to, those ingredients described in Remington: The Science and Practice of Pharmacy, Lippincott Williams & Wilkins, 21st ed. (2006) (hereinafter Remington's).

The compounds may be combined with a fine inert powdered carrier and inhaled by the subject or insufflated. Such compositions and preparations should contain at least 0.1% compounds. The percentage of the compositions and preparations may, of course, be varied and may conveniently be between about 2% to about 60% of the weight of a given unit dosage form.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. A syrup or elixir may contain the active compound, sucrose or fructose as a sweetening agent, methyl and propylparabens as preservatives, a dye and flavoring such as cherry or orange flavor.

Various other materials may be present as coatings or to otherwise modify the physical form of the solid unit dosage form. For instance, tablets, pills, or capsules may be coated with gelatin, wax, shellac or sugar and the like. Of course, any material used in preparing any unit dosage form should be pharmaceutically acceptable and substantially non-toxic in the amounts employed.

In addition, the compounds may be incorporated into sustained-release preparations and devices. For example, the compounds may be incorporated into time release capsules, time release tablets, and time release pills. In some embodiments, the composition is administered using a dosage form selected from the group consisting of effervescent tablets, orally disintegrating tablets, floating tablets designed to increase gastric retention times, buccal patches, and sublingual tablets.

The compounds may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include conventional nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the compounds can be determined by comparing their in vitro activity, and in vivo activity in animal models. Methods for the extrapolation of effective dosages in mice, and other animals, to humans are known to the art.

For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g, The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The compounds are conveniently administered in unit dosage form; for example, containing 0.05 to 10000 mg, 0.5 to 10000 mg, 5 to 1000 mg, or about 100 mg of active ingredient per unit dosage form. In some embodiments, the dosage unit contains about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 750 mg, or about 1000 mg of active ingredient.

Further aspects and embodiments of the invention are disclosed in the following examples. Briefly, the examples show that strands F and H are actively involved in TTR aggregation, and disclose a new strategy for the inhibition of TTR aggregation by specific binding of small peptides to these protein segments that are necessary for aggregation. In various embodiments, one or two inhibiting peptides are used in drugs and other compositions of matter against TTR systemic diseases.

EXAMPLES

Example 1: Ex-Vivo Seeds Extracted from ATTR-D38a Cardiac Tissue Cause TTR Fibril Formation We extracted amyloid fibrils from the explanted heart of a hereditary transthyretin amyloidosis (ATTR) patient carrying the ATTR-D38A mutation. Our procedures for extraction and characterization are outlined in FIG. 1A. Prior to extraction, we confirmed the amyloid content of the explanted heart by Congo red and immuno-staining of paraffin embedded sections of the organ (FIGS. 1, B and C). Sections stained with Congo-red displayed streaks of apple-green birefringence (FIG. 1B). Tissue immunostaining revealed the presence of scattered patches of TTR deposits throughout the sample (FIG. 1C). The amyloid extraction was performed on a 1-5 g frozen piece from the same organ by the protocol of Westermark et al. (34), using multiple cycles of homogenization with saline and water. We confirmed the presence of both short and long amyloid-like fibrils in the resultant resuspension by electron microscopy (FIG. 1D). The ex-vivo amyloid fibril resuspension exhibits the cross beta diffraction pattern when exposed to an x-ray beam (FIG. 1E). The presence of TTR in the sample was confirmed by western blot and mass spectrometry-based protein sequencing (FIG. 1F).

We next studied the ability of the ex-vivo amyloid material to seed soluble, tetrameric TTR. We define as "seeds" ex-vivo material obtained from ATTR patients that can accelerate recombinant TTR fibril formation. Ex-vivo ATTR seeds were obtained from the fibril resuspension after a mild detergent washing treatment and 5 minutes of sonication as outlined in FIG. 1A. Total protein concentration was measured and increasing amounts of ex-vivo seeds (0-50 ng/µl) were added to native recombinant TTR at a concentration of 0.5 mg/ml. Two forms of recombinant TTR were studied in this assay: wild type TTR and the variant D38A mutant. Fibril formation was followed by Thioflavin T (ThT) fluorescence at 37° C. with constant orbital shaking. While ex-vivo seeds alone did not result in any significant increase of ThT signal, fluorescence peaked after a lag phase of 10 to 20 minutes when recombinant D38A mutant or wild type protein was added (FIGS. 1, G and H). Recombinant transthyretin alone did not cause an increase in ThT signal in the absence of ex-vivo seeds (FIGS. 1, G and H). After 24 hours, the samples were collected and analyzed by electron microscopy, revealing fibrillar structures (FIG. 10).

We confirmed that the resultant fibrils derived from de-novo fibril formation from recombinant protein as follows. First, we obtained the insoluble fraction of the samples by centrifugation and resuspension in guanidinium hydrochloride. These fractions were spotted onto a nitrocellulose membrane for immuno-dot blot analysis with an antibody that recognizes the histidine tag of recombinant protein. We found a seed-dependent enhancement of recombinant TTR content in the insoluble fraction (FIG. 1J), consistent with an increase of absorbance at 280 nm (FIG. 1K). As expected, the increase of insoluble material was accompanied by a gradual decrease of soluble TTR, as detected by BCA protein assay and western-blot. We could not detect any remaining soluble protein after 24 hours incubation with seeds at 30 ng/µl or higher. Experiments confirm that the seeding effect is dependent on the addition of ATTR seeds. In this experiment, we added 30 ng/µl seeds to recombinant wild type TTR after 20 hour pre-incubation. Before the addition of seeds, the sample was ThT-negative and did not contain any visible sign of aggregation. The addition of seeds resulted in a rapid increase of ThT signal which correlates with the accumulation of protein aggregates visualized by optical microscopy. Additionally, we found that gradual addition of recombinant protein (0 to 1 mg/ml) to a fixed amount of seeds (30 ng/µl) results in a TTR-dependent seeding effect. Taken together, these results indicate that ex-vivo extracts obtained from ATTR-D38A cardiac tissue can accelerate fibril formation of recombinant wild type and D38A TTR.

As a negative control, we obtained cardiac tissue explanted after ATTR-unrelated heart failure. We confirmed the absence of amyloid TTR deposits by Congo red and immuno-staining of tissue sections. After performing the saline-water extraction described above, we evaluated TTR content in the extract by anti-TTR dot blot, and confirmed the absence of amyloid fibrils by electron microscopy. We then performed an amyloid seeding assay as described above, and found that non-ATTR ex-vivo extract does not accelerate native recombinant TTR fibril formation. These results indicate that TTR amyloid seeding is not caused by insoluble material extracted from any cardiac specimen, such as collagen.

We next confirmed that amyloid seeding was caused by the TTR fibrillar content of ex-vivo extracts and not by other co-extracted insoluble material. We first observed that sonication greatly potentiates TTR amyloid seeding, suggesting the involvement of fibril tips in templating TTR fibril formation. In addition, we immunodepleted ex-vivo extracts of TTR and tested their capacity to seed recombinant wild type TTR. First, we sequentially removed TTR from the ex-vivo extract by several cycles of binding to an anti-TTR surface. We then assayed the remaining material and found that the seeding capacity becomes diminished by gradually removing TTR from the extract. These findings suggest that amyloid seeding of recombinant TTR is caused by fibrillar TTR-derived material found in ATTR cardiac tissue.

ATTR-D38A seeds accelerate fibril formation of other recombinant variants. When added to two recombinant familial variants, V30M and L55P, ex-vivo seeds enhanced amyloid fibril formation. While we did not detect any ThT signal increase in the absence of seeds, the addition of 30 ng/μl ATTR-D38A ex-vivo seeds resulted in the formation of ThT-positive species for both familial variants. Although the insoluble fraction collected after 24 hours contained transthyretin when incubated without seeds, we found that this insoluble material contained mainly amorphous aggregates when analyzed by electron microscopy, in contrast to fibrillar structures found when incubated with seeds.

Example 2: Seeded TTR Fibrils Exhibit Amyloid-Like Features

Seeded TTR fibrils and ex-vivo seeds both display the cross beta diffraction pattern when exposed to x-rays (FIG. 1E). The diffraction patterns of both fibrils exhibit the two characteristic strong reflections of amyloid: the reflection at 4.7 Å results from the stacking of β-strands along the fibril, and the reflection at near 11 Å results from the separation of adjacent β-sheets. Circular dichroism analysis suggests a beta-rich secondary structure in both fibrils. We also found that both fibrils exhibit birefringence when stained with Congo-red. Unlike non-seeded aggregates from recombinant protein, seeded fibrils and ex-vivo seeds share fibrillar morphology when observed by electron microscopy (FIG. 1I), and similar oligomeric composition when analyzed by western blot without boiling the samples (FIG. 1F). Taken together, our results indicate that: (i) ex-vivo amyloid seeds accelerate fibril formation of not only recombinant familial variant TTR but also wild type TTR, and (ii) both ex-vivo seeds and seeded fibrils share amyloid-like features.

Example 3: ATTR Material from Various Genotypes Also Seed TTR Fibril Formation

Ex-vivo material extracted from the hearts of seven additional ATTR patients were also capable of seeding fibril formation of TTR (FIG. 2A). Among these patients, there were three cases of wild type amyloidosis and four cases of hereditary amyloidosis, other than ATTR-D38A. Superscripts are used to differentiate ATTR patients with the same genetic background. All patients presented advanced amyloidosis symptomatology or are deceased as a consequence of ATTR. The tissue specimens came from either explanted or autopsied hearts. We confirmed the presence of amyloid-like fibrils after the extraction by electron microscopy. We also confirmed TTR content in the resultant fibril resuspension by western-blot and mass-spectrometry sequencing. We found that the ex-vivo seeds extracted from the hearts of these seven patients cause amyloid fibril formation of recombinant wild type TTR, as we observed for ATTR-D38A ex-vivo seeds (FIG. 2A).

We next analyzed whether there is a correlation between amyloid seeding capacity with any of cardiac pathology subtype, gender or age, three factors previously associated with ATTR severity (35-37). The presence of fragmented TTR, present in type A cardiac amyloidosis, was evaluated by western blot using an antibody that specifically recognizes TTR C-terminal fragments. With the exception of ATTR-T60A, we observed an apparent correlation between seeding capacity and fragmented TTR content, with a Pearson correlation coefficient of 0.96 (FIG. 2B). We did not observe correlation with ATTR patient age or gender in our assays (FIG. 2C). However, these findings should be further evaluated in a larger cohort.

We made additional observations about amyloid seeding caused by cardiac ATTR seeds. As expected from Kelly's discoveries (38), we found that amyloid seeding of ex vivo fibrils required some degree of protein denaturation by pH, with the greatest fibril formation at pH 4.3. Similar to ex vivo fibrils, seeded fibrils were also found to cause fibril formation of recombinant wild type TTR, indicating that the conformation of the ex vivo fibrils is encoded in the products of the fibril formation assay. We also found that both ex-vivo seeds and seeded fibrils share a similar protease-resistant core. Protease digestion of type A ATTR-D38A seeds or seeded fibrils resulted in the appearance of a ~9.5 kDa fragment, while type B ATTR-WT$^2$ seeds or seeded fibrils resulted in the appearance of a total of three fragments of 10, 12, and 20 kDa, approximately.

Example 4: Stabilizing Native TTR Fails to Halt Amyloid Formation Induced by Disease-Related Seeds Next we tested the ability of compounds and mutations that stabilize native, tetrameric TTR to halt amyloid formation induced by disease-related amyloid seeds. Extensive biochemical studies have led to the discovery of compounds such as tafamidis and diflunisal that bind within the tetrameric structure of TTR and stabilize the native structure, inhibiting its fibril formation (23, 24, 39). Consistent with these studies, we found that both tafamidis and diflunisal efficiently inhibit recombinant TTR aggregation in vitro (FIGS. 3, A and B). For these aggregation assays, we incubated 1 mg/ml recombinant wild type TTR with increasing amounts of stabilizers. After 4 days in the absence of inhibitor, virtually the total amount of TTR present was converted to aggregates. In the presence of either tafamidis or diflunisal, TTR aggregation became considerably diminished in a dose-dependent manner (FIGS. 3, A and B). However, their presence did not reduce or delay fibril formation when ATTR-D38A ex-vivo seeds were added to 0.5 mg/ml recombinant TTR, even at compound concentrations that previously resulted in full inhibition of TTR aggregation (FIGS. 3, C and D).

After evaluating tetramer stabilization on the inhibition of the seeding potential of ex-vivo ATTR-D38A fibrils, we expanded our study to seeding material extracted from cardiac tissue of other patients. We found that the presence of tafamidis or diflunisal in the assay did not result in the reduction of the accumulation of insoluble material (FIG. 3E). These findings indicate that tetramer stabilization by compounds appears insufficient to halt amyloid seeding.

We then evaluated tetramer stabilization by mutagenesis, analyzing the effect on amyloid seeding of the tetrameric form of the T119M TTR variant. This variant exhibits high tetrameric stability that results in significant delay of the onset of familial neuropathic ATTR in patients who carry both V30M and T119M variants (23, 40). We found that although the recombinant T119M variant remained soluble after days of incubation at the low pH which causes native TTR to dissociate (32) (FIG. 3F), the addition of ATTR-D38A ex-vivo seeds did indeed cause fibril formation with a short lag phase of 10 to 20 minutes (FIG. 3G). Notably, unlike T119M, the TTR variant T119W, which blocks self-association of the strand H, did show a significant decrease of protein fibril formation upon seeding (FIGS. 3, F and G). We also found that although ex-vivo seeds caused the aggregation of a TTR variant that blocks self-association of the strand F, S85P/E92P, the lag phase was significantly longer (FIG. 3G). These findings suggest that increasing the stability of the tetrameric form of transthyretin is not sufficient to stop fibril formation when seeds are present. Instead, the results indicate that blocking self-association of amyloidogenic TTR strand H may be a more effective approach (FIG. 3G).

Example 5: Amyloid Seeding can be Halted by Transthyretin Aggregation Blockers

Having established the power of ex-vivo TTR fibrils to seed even stabilized native TTR into fibrils, we evaluated the inhibitors of TTR aggregation that emerged from our previous studies (32). In that work we identified β-strands F and H of native TTR as being required for TTR amyloid aggregation in vitro. From the atomic structures of these strands in their amyloid forms we designed two 16-residue peptides intended to cap fibrils of the F and H strands. Together these two peptides were able to reduce fibril formation of wild type TTR.

In the present work, we optimized these peptides by reducing their amyloidogenicity without compromising their inhibiting activity, as detailed in Materials and Methods. All evaluated sequences including both original and optimized peptides are listed in Table 1. We then evaluated the effectiveness of the best scored inhibitors in our seeding assays (FIG. 4A and Table 1). We found that two optimized peptides did indeed halt TTR fibril formation more efficiently than our earlier inhibitors (FIG. 4A). Both original and optimized peptide inhibitors are named as Tab (Transthyretin aggregation blockers) followed by the letters F and/or H referring to the target strand(s). The name ends with a number that depends on whether the peptide was obtained in the original design (32) (number 1) or optimized in the present work (number 2). For instance, TabF1 corresponds to the peptide inhibitor that targets strand F as described in Saelices et al., 2015, and TabFH2 refers to a cocktail of the two optimized peptide inhibitors that target strands F and H designed and characterized in this study (Table 1). In our amyloid assays, we found that targeting strand H is more effective than strand F (FIG. 4A). Nonetheless, the combination of peptide blockers for both strands F and H, TabFH2, resulted in full inhibition of seeding from ex-vivo ATTR-D38A fibrils (FIG. 4A).

We then confirmed the ability of TabFH2 to bind ATTR seeds (FIG. 4B). To detect binding of TabFH2 to ATTR seeds, we first immobilized 5 µg of ATTR-D38A seeds on each of eight anti-TTR pre-coated wells. Binding of ATTR seeds to the bottom of the wells was confirmed later by BCA protein assay. We then added increasing amounts of TabFH2 (0-500 µM) to pretreated wells. After 2 hour incubation, we analyzed the remaining amount of TabFH2 in the sample by HPLC. Anti-TTR pre-coated wells treated with buffer, but not seeds, were used as negative control to detect unspecific binding of TabFH2 to the well. While the majority of TabFH2 remained in the sample after incubation in negative control wells, most of TabFH2 was absent when wells were pretreated with ATTR seeds (FIG. 4B). Our results show that TabFH2 efficiently binds ATTR ex-vivo seeds.

We found that TabFH2 halts amyloid seeding caused by ex-vivo seeds extracted from all ATTR cases evaluated (FIG. 4C). The efficacy of TabFH2 was dose-dependent, and although its efficiency differs from sample to sample, full inhibition was observed at the highest concentration analyzed (FIG. 4C). This variability did not show association with mutational background of the ex-vivo seeds. Instead, we found an inverse relationship between TabFH2 effectiveness and the amount of TTR C-term fragments found in the ex-vivo resuspension. Pearson's correlation coefficient between amyloid seeding in the presence of 180 µM TabFH2 and TTR fragment content was of 0.90 (R-square=0.80) indicating a positive correlation.

Further evidence that TabFH2 efficiently inhibits amyloid seeding comes from the following experiment. We extracted ex-vivo seeds from small quantities of adipose tissue obtained by tissue biopsies of ATTR patients to evaluate tissue specificity of TabFH2. Among the five biopsied patients, there was one case of wild type ATTR, and four cases of hereditary ATTR. Since the adipose specimens were considerably smaller than the cardiac tissue samples (30-150 mg vs 1-5 g), we downsized the amyloid extraction protocol accordingly. Otherwise, the procedure remained as described above. We confirmed the presence of insoluble transthyretin in the resulting resuspension by western-blot using two anti-TTR specific antibodies. The extraction produced a very limited amount of insoluble material. We were therefore forced to reduce to 5 ng/µl the amount of ex-vivo seeds used in amyloid seeding assays. The ThT signal was insufficient to draw any conclusion even after 7 days incubation time. Therefore, we opted to follow amyloid seeding by image-based computational quantification of protein aggregates after 24 hours of incubation. We collected images of the bottom of 96 well plates by optic microscopy using the Celigo S Imaging system. The images showed formation of UV-positive aggregates in those samples that contained ex-vivo seeds and no apparent aggregation in the control samples. The inhibitory effect of TabFH2 was confirmed by showing a significant reduction of amyloid conversion at 180 µM (FIG. 4D). It is worth mentioning that five additional biopsy samples showed no trace of TTR after extraction, and they did not cause aggregation of recombinant TTR, thereby supporting our previous observation that the presence of TTR material in the extract is necessary to cause seeding. Taken together, our results indicate that TabFH2 efficiently inhibits amyloid seeding caused by wild type and mutant ex-vivo seeds in a tissue-independent manner. These studies encouraged us to evaluate our inhibitors in vivo.

Example 6: Assessment of the Effects of TABFH2 on Motor Skills in ATTR *Drosophila* Models We tested our seeding inhibitors TabFH2 in two *Drosophila* models of ATTR. The expression and aggregation of human mutant TTR in the fruit fly results in reduction of both lifespan and climbing ability (41-43). To evaluate the efficacy of TabFH2 in vivo, we made use of two *Drosophila* models carrying the following backgrounds: (i) the strain TTRV30M, expressing the familial TTR mutant V30M (43); and (ii) the strain TTR-A, expressing an engineered TTR variant carrying the double mutation V14N/V16E (41). After eclosion, flies were fed with vehicle, TabFH1, or TabFH2 at two different concentrations. Peptide incorporation in the flies was confirmed by mass spectrometry. Peptides were detected in the bodies of the flies in a dose-dependent manner. We could not detect peptides in the heads of the flies, perhaps because of insufficient sensitivity of the procedure or because peptides bound to insoluble TTR deposits are discarded prior to mass spectrometry analysis. The effect of TTR blockers on fly mobility was evaluated in climbing assays. Oregon wild type flies were included as healthy controls. TabFH1 was included in the analysis to confirm optimization and rule out nonspecific effects of peptide-based treatment. TTR-expressing vehicle-treated flies were used as negative controls. Flies were analyzed in climbing assays at different time points, along with a survival analysis. Neither TabFH1 nor TabFH2 resulted in a significant change of survival. Ten flies of each genotype or drug treatment were placed in plastic vials in replicates and allowed to climb, and several locomotor paradigms were assessed. For both genotypes, TabFH2-treated flies showed significant relative motor improvement in several measures, including traveled distance, climbing velocity, and overall time of flies in motion (FIG. 5). This improvement was accompanied with a dose-dependent reduction of TTR deposition as monitored by western blots of head homogenates after 17 days of treatment (FIG. 5C).

Example 7: Illustrative Materials and Methods

Antibodies used were rabbit anti-human transthyretin polyclonal antibody (DAKO, Agilent Technologies; fly head homogenate western blots, 1:2,000; other western blots and dot blots, 1:10,000; immunohistochemistry, 1:2,000; ELISA, 1:4,000) and horseradish peroxidase-conjugated goat anti-rabbit IgG antibody (DAKO, Agilent Technologies; western blots and dot blots, 1:5,000; immunohistochemistry, 1:2000; ELISA, 1:1,000). Anti-truncated TTR was obtained as a gift from Gunilla Westermark (72) (labeled as 1898; 1:5,000).

Eighteen ATTR patients carrying wild type (n=4) or TTR mutations (n=14) were included in the study. Cardiac specimens were obtained from several laboratories either from explanted heart or autopsy. Adipose aspirates were obtained through a needle biopsy performed in the University Medical Center Groningen. The study was approved by the ethical committees of the respective laboratories and universities.

Congo red staining was performed to verify the presence of amyloid deposition in tissues. Abdominal fat tissue smears were prepared on probe-on microscope slides. 10 µm thick cardiac sections were deparaffinized by heating, xylene baths, and gradual hydration. The samples were stained using the Amyloid Stain, Congo Red kit (Sigma Aldrich) as described by the manufacturer. Briefly, slides were incubated in a freshly made alkaline sodium chloride solution for 30 minutes, and then transferred to and incubated in an alkaline Congo red solution for another 30 minutes. Slides were dehydrated and mounted with Permount, then analyzed under bright field and polarized light. Amyloid was identified by its characteristic apple-green birefringence.

Immuno-staining of 4 µm tissue sections was performed using polyclonal rabbit anti-human transthyretin antibodies (DAKO, Agilent Technologies), or immunoglobulin fraction from non-immunized rabbits as negative control (DAKO, Agilent Technologies) diluted 1:2000 in blocking buffer. Horseradish peroxidase-conjugated goat anti-rabbit IgG antibody (DAKO, Agilent Technologies) was used diluted 1:2000 in blocking buffer. Reactivity visualization was made with the EnVision™+ System/HRP, Rb (DAB+) (DAKO, Agilent Technologies) as described by the manufacturer.

Abdominal fat smears were made as previously described (73). Slides were stained with alkaline Congo red (74) and apple-green birefringence under polarized light were semi-quantitatively scored as follows: 0 (negative), 1 (minute, <1% surface area), 2 (little, between 1 and 10%), 3 (moderate, between 10 and 60%), and 4 (abundant, >60%). The remaining abdominal fat tissue was weighted and washed. Proteins were resuspended with a tris-guanidine solution, and TTR content was measured by ELISA. Briefly, microtiter plates were coated overnight with the extracts and human native TTR protein (Abcam, Cambridge, UK), which served as control, in several dilutions. Detection was done by using rabbit anti-human TTR polyclonal antibodies (DAKO, Agilent Technologies) followed by horseradish peroxidase-conjugated goat anti-rabbit IgG antibody (DAKO, Agilent Technologies) and visualized by a color reaction with TMB Elisa substrate. Plates were scanned at 450 nm after stopping the reaction with sulfuric acid.

Amyloid fibrils were extracted from fresh-frozen human tissue as described earlier (34). Briefly, 1-5 g of amyloid-positive cardiac tissue was thawed and minced with a modular motorized homogenizer in 10 ml of 0.15 M NaCl. Due to the small amount of tissue contained in fat biopsies (30-200 mg), the volume was downsized accordingly. The sample was centrifuged at 15,000 rpm for 30 minutes and the resulting pellet was homogenized in 0.15 M NaCl and centrifuged again. This process was repeated 7 times. The pellet was further homogenized in distilled water, centrifuged three times and the final pellet was lyophilized. Amyloid fibril load was confirmed by electron microscopy and x-ray fiber diffraction. Transthyretin content was analyzed by western-blot and LS-ESI-MS/MS. Non-ATTR cardiac control tissue was subjected to the same extraction procedure.

TTR aggregation was confirmed by TEM as described in Saelices et al. (32). Briefly, 5 µl sample was spotted onto freshly glow-discharged carbon-coated grids (Ted Pella, Redding, Calif.), incubated for 3 minutes and then rinsed three times with distilled water. Grids were finally negatively stained with 2% uranyl acetate for 2 min. A T12 Quick CryoEM electron microscope at an accelerating voltage of 120 kV was used to examine the specimens. Images were recorded digitally by a Gatan 2k×2k CCD camera.

X-ray fibril diffraction patterns were collected as described previously (75). Briefly, seeded fibrils and ex-vivo extracted fibrils were concentrated by centrifugation, washed, and oriented while drying between two glass capillaries. The glass capillaries were mounted on a brass pin for diffraction at room temperature using x-rays produced by a Rigaku FRE+ rotating anode generator equipped with an HTC imaging plate. Diffraction patterns were collected at a distance of 180 mm and analyzed using the Adxv software package (76). Pixel intensity densities were calculated by ImageJ (77) and x-ray reflection peaks were obtained by radial intensity averaging.

Ex-vivo seeds were analyzed by mass spectrometry before and after detergent treatment, as described elsewhere (78). Briefly, the detergent treatment was performed as follows. Samples were sonicated in 10 volumes of buffer A (10 mM Sodium Acetate pH 7, 100 mM KCl, 10 mM EDTA), and the homogenate was centrifuged at 800×g for 10 min. The supernatant was treated with $\frac{1}{10}$ volume of buffer A containing 10% of Nonidet P-40. This solution was mixed well, sonicated, and centrifuged at 100,000×g. An additional, harsher detergent extraction was performed on the pellet by resuspension in 1 ml of buffer A with 0.5% Nonidet P-40, 0.25% SDS, and 0.5% deoxycholate. This homogenate was sonicated and centrifuged at 100,000×g for 30 min. The resulting pellet was also subjected to an additional washing step in 1 ml of buffer A with 0.5% Nonidet P-40, 0.25% SDS, and 0.5% deoxycholate, and then sonicated at centrifuged at 100,000×g for 30 min. The supernatants were saved and further analyzed. For storage and analysis, the washed final pellet was resuspended in 200 µl of water and kept at ~80° C.

Prior to the trypsin digest, a chloroform/methanol precipitation was performed to precipitate the protein in the original ex-vivo seeds, supernatants, and detergent-insoluble pellets. Four volumes of methanol, one volume of chloroform, and three volumes of water were sequentially added to one volume of each protein sample, and vortexed after each addition. The samples were centrifuged at 16,000×g for 5 minutes and the aqueous supernatant was removed. The protein remained at the interface between the upper and lower phases. Four volumes of methanol were again added, and the samples were vortexed. The samples were centrifuged at 16,000×g for 5 minutes and the supernatant was removed without disturbing the pellet. The protein pellets in each sample were solubilized in an in-solution digest buffer consisting of 0.5% sodium deoxycholate, 12 mM sodium lauroyl sarcosinate, 50 mM triethylammonium bicarbonate (TEAB). Samples were heated for 5 minutes at 95° C. and the protein concentrations were measured using the Pierce™ BCA Protein Assay Kit (ThermoFisher Scientific). Protein disulfides were then reduced with 5 mM tris(2-carboxyethyl) phosphine (TCEP) in 50 mM TEAB for 30 minutes at room temperature, and alkylated with 10 mM iodoacetamide in 50 mM TEAB for 30 minutes at room temperature in the dark. Protein solutions were diluted five-fold with 50 mM TEAB. Lyophilized porcine trypsin (Promega, Madison, Wis., USA) was solubilized in 50 mM TEAB, and used in a mass ratio of 1:100 (trypsin:protein) for a double enzymatic digestion of 4 hours and then over/night at 37° C. Sodium deoxycholate was precipitated from the peptide solutions with triflouroacetic acid at a final concentration of 0.5%. The samples were then centrifuged at 16,000×g for 5 minutes and the supernatant was transferred into new tubes prior to lyophilization in a centrifugal evaporator. The samples were then reconstituted in 100 μl of a buffer solution (2% acetonitrile, 0.5% acetic acid) and desalted with c18 stage tips as previously described elsewhere (79). Eluted samples were lyophilized and solubilized with 10 μl of 2% acetonitrile, 0.1% formic acid, which was then placed into injection vials for MS analysis.

The samples were analyzed with an Eksigent 2D nanoLC attached to a Q-Exactive Plus (ThermoFisher Scientific). Peptides were injected onto a laser pulled nanobore 20 cm×1.8 μm c18 column (Acutech Scientific, San Diego, Calif., USA) in buffer A (2% acetonitrile, 0.15% formic acid), and eluted using a 3 hour linear gradient from 3-80% buffer B (98% acetonitrile, 0.15% formic acid). The Q-Exactive plus was operated in Full MS/dd-MS2 mode with resolution of 70,000 and an auto gain control target of 3e6 for the parent scan. The top 20 ions above +1 charge were subjected to higher collision dissociation (HCD) set to a value of 30 with a resolution of 17,500 and an auto gain control target of 1e5 as well as a dynamic exclusion of 15 seconds. Tandem mass spectrometry data was matched to against a protein fasta file (UniProt-Human 20161005 21,047 sequences; 11,462,872 residues) using Mascot software (Matrix Sciences, Boston, Mass.). Identified proteins are listed in Supplemental Material, ordered by exponentially modified protein abundance index (emPAI). emPAI offers approximate, label-free, relative quantitation of the proteins in the mixture based on protein coverage by the peptide matches in the database search result. All ex-vivo extracts were enriched in transthyretin, but also contained a mixture of other proteins, with the consistent presence of serum amyloid-P component, myosin, collagen and a TRAJ56 fragment.

Equal amounts of total protein were loaded and separated by electrophoresis in denaturing conditions, and immunoblotted with polyclonal anti-human transthyretin (DAKO, Agilent Technologies, 1:10,000) or anti-truncated TTR obtained from Gunilla Westermark (1:5,000). Horseradish peroxidase-conjugated goat anti-rabbit secondary antibody was diluted to 1:5,000 and SuperSignal™ West Pico Chemiluminescent Substrate (ThermoFisher Scientific) was used to detect transthyretin as described by the manufacturer. Intensity quantification was performed by ImageJ (77) from at least two independent blots.

Recombinant protein preparations were obtained as described previously (32). Briefly, E. coli expressed proteins were purified by affinity in a Histrap column (GE Healthcare Life Science). Peak fractions were combine and further purified by size exclusion in a Superdex S75 prep grade column (GE Healthcare Life Science). Final samples were stored in 10 mM sodium acetate pH 7.5, 100 mM KCl, 10 mM EDTA at −20° C.

TTR aggregation assays are described previously (32). Briefly, 1 mg/ml TTR sample in 10 mM Sodium Acetate pH 4.3, 100 mM KCl, 10 mM EDTA was incubated at 37° C. for a maximum of 4 days. Protein aggregation was followed by absorbance at 400 nm, anti-TTR immuno-dot blot of the insoluble fraction, and/or transmission electron microscopy.

Fibril extracts were used to seed the formation of new aggregates from recombinant TTR. In order to further purify the extracts, they were treated with 1% sodium dodecyl sulfate and the soluble fraction was discarded after centrifugation at 13,000 rpm for 5 minutes. This process was repeated two times. The sample was washed with distilled water three times by centrifugation, and then sonicated in cycles of 5 seconds on, 5 seconds off, for a total of 10 minutes, at minimum intensity (18%). The protein content was measured using the Pierce™ BCA Protein Assay Kit (ThermoFisher Scientific). Seeds were added to 0.5 mg/ml recombinant TTR in a final volume of 200 μl of 5 μM thioflavin T, 10 mM Sodium Acetate pH 4.3, 100 mM KCl, and 10 mM EDTA. Unless labeled otherwise, cardiac seeds were analyzed at 30 ng/μl concentration and seeds extracted from adipose tissue were analyzed at 5 ng/μl. Thioflavin fluorescence emission was measured at 482 nm with absorption at 440 nm in a Varioskan Flash (ThermoFisher Scientific) or FLUOstar Omega (BMG LabTech) plate readers. Plates were incubated at 37° C. for 20-72 h as labeled with cycles of 9 min shake (700 rpm double orbital) and 1 min rest throughout the incubation. Measurements were taken with automatic gain if read in Varioskan Flash, or with a manual gain of 1,000 if read in FLUOstar Omega, every 10 min, bottom read. We normalized all our assays by subtracting ThT signal at initial point of incubation. Figures show ThT signal in arbitrary units (a.u.). Fibril formation was confirmed by TEM. Insoluble fraction was extracted by two cycles of centrifugation with buffer A, and final resuspension with 6M Guanidinium Hydrochloride. Soluble fractions were saved from the first centrifugation cycle and protein concentration was measured by Pierce™ BCA protein assay kit (ThermoFisher Scientific). Absorbance at 280 nm of insoluble fractions was measured in absorbance units (AU) in a BioPhotometer UV/Vis Spectrophotometer (Eppendorf) or in a Nanodrop 1000 (ThermoFisher Scientific). Insoluble and soluble fractions were further analyzed by immuno blots.

Samples containing 0.5-1 μg of recombinant wild type, ATTR seeds, or seeded fibrils that resulted from 24 hour incubation of 0.5 mg/ml recombinant wild type with 30 ng/μl ATTR seeds, were incubated with proteinase K at several concentrations (0, 0.03, 0.3 and 3 ng/μl) in 30 mM Tris-HCl, 30 mM EDTA, for 3 hours at 37° C. Two ATTR seeds and seeded product were analyzed: ATTR-D38A and ATTR-WT$^2$. Protein was resolved on NuPAGE® Novex® 4-12% Bis-Tris Protein Gels in MES SDS running buffer, and stained with silver using a Pierce™ Silver Stain Kit (ThermoFisher Scientific), following manufacturer's directions. Grey intensity profiles of gel lanes were obtained by ImageJ and plotted by Prism.

TTR fibrils were depleted from ex-vivo extract by immunoreaction to anti-TTR microplate strips from Prealbumin ELISA kit (Abcam) as follows. 100 µl sample containing 1.2 µg/µl ATTR-D38A was added to an anti-TTR pre-coated well and incubated at room temperature for 30 minutes. The sample was transferred to a new well and incubated again at room temperature for 30 minutes. This procedure was repeated 8 times. After every incubation, 5 µl aliquots were transferred to test tubes and saved. A 5 µl aliquot was also collected from the original sample, prior to incubation. Amyloid seeding assay was performed as described above. Collected samples were added to 0.5 mg/ml recombinant wild type transthyretin in a final volume of 200 µl and ThT fluorescence was read in FLUOstar Omega, every 10 min for 24 hours, with a manual gain of 1,000. Optic micrographs of resulting aggregates were taken after incubation using a Celigo S Imaging system under bright field and UV channels.

TTR aggregation was visualized by dot-blot analysis as described previously (32). The insoluble fraction of the samples was obtained by cycles of centrifugation as described above, and dotted onto nitrocellulose membranes (0.2 µm, Bio-Rad). TTR was observed by using HisProbe or polyclonal rabbit anti-human transthyretin (DAKO) antibodies at a concentration of 1:10,000.

Secondary structures of ATTR seeds or seeded fibrils were analyzed by circular dichroism (CD) spectroscopy. Samples (200 µl) were placed into a 1-mm path length quartz cell (Hellma Analytics). A Jasco J-810 UV-Vis spectropolarimeter was employed. Spectra were obtained in a wavelength range of 195 to 260 nm, with a time response of 2 s, a scan speed of 50 nm/min, and a step resolution of 0.2 nm. Each spectrum was the average of ten accumulations. All the samples were assayed at a concentration of 0.5 mg/ml in buffer A. Fibril samples were centrifuged and washed with Buffer A twice, and then sonicated in a bath for 2 minutes prior to measurement. Spectra were recorded at 25° C. The results are expressed as measured ellipticity (mdeg). The ellipticity of the samples was normalized by using the ellipticity of Buffer A as a blank. The estimated percentage of various structural conformations was calculated by Bestsel (80). Ellipticity of ex-vivo seeds was processed considering the sample to be monodisperse TTR material.

A first generation of TTR aggregation blockers were designed to bind strands F and H as described previously (32). They shared a 12-residue-long wild type sequence with the addition of an N-methyl group and a four-residue arginine-tag (SEQ ID NO: 69). The use of the non-natural N-methyl groups to protect aggregation blockers from proteolysis has been reported elsewhere (81). The addition of a poly-arginine tag confers higher solubility that is presumed to hinder self-aggregation. These peptides were further optimized in silico to decrease potential self-association. Two in silico optimization strategies were performed. (i) Each residue of each peptide was subsequently substituted by arginine, and (ii) the overall composition of the peptides was maintained, but the order of residues was changed. The overall propensity to form steric zippers of every sequence was calculated by the algorithm ZipperDB, developed previously in our laboratory (82, 83). ZipperDB calculates the propensity of each 6 residue segment, of any given sequence, to form steric zippers. Predicted full-atom energy of interactions across the zipper interface formed by possible self-association for each peptide inhibitor is shown in Table 1. We found that arginine substitutions did not result in a significant energy difference (Table 1). Sequence swapping resulted in peptide sequences with the highest energy scores, which were less prone to aggregate. The C-terminal residue of F15 was eliminated to obtain a higher energy score resulting in TabF2. The optimized inhibitors were then selected and tested in vitro.

The best scoring peptides were evaluated in vitro for their efficacy at inhibiting amyloid seeding (Table 1). Amyloid seeding assays were performed as described above. 180 µM peptide was added to 0.5 mg/ml recombinant wild type TTR and 30 ng/µl ATTR-D38A seeds. Amyloid seeding was measured after 24 hour of incubation at 37° C. by ThT fluorescence. Thioflavin T signal obtained in the absence of peptide was considered 100%. The best two inhibitors, TabF2 (RRRRHVAHPFV-N-me-Glu-FTE (SEQ ID NO: 72)) and TabH2 (RRRRSYVTNPTSY-N-me-Ala-VT (SEQ ID NO: 73)) were selected for further analysis and used as a cocktail, here referred as TabFH2.

TabFH2 binding to ATTR seeds was analyzed by HPLC. First, ATTR-D38A fibrils were immobilized on anti-TTR pre-coated well plates (Prealbumin ELISA kit, Abcam) as follows. 50 µl samples containing 0.1 µl ATTR seeds were added on each well. Control wells were equally treated with Buffer A. After 1 hour incubation at room temperature, samples were then removed and wells were washed twice with Buffer A. Immobilization of the total amount of fibrils was confirmed by BCA protein assay of the remaining sample. 50 µl samples that contained increasing concentrations of TabFH2 (0-500 µM) were added to independent wells pretreated with ATTR seeds or buffer. After an incubation of 2 hours at room temperature, samples were transferred to new tubes and snap frozen until further analysis. Unbound TabFH2 was detected by chromatography after 0.10 nm filtration, on an Waters 1525 HPLC System (SpectraLab), with a Proto 300 C18 5 µm 250×4.6 mm analytical reverse phase column (Higgins Analytical). Flow rate=1.0 ml/min; solvents: A=0.1% trifluoroacetic acid in water, and B=0.1% trifluoroacetic acid in acetonitrile. The column was equilibrated with 10% B for 5 minutes, followed by a gradient from 10% to 60% B in 30 minutes, and a 2 minute wash at 95% B. TabFH2 eluted in two peaks after approximately 17 and 20 min from start. Peaks were integrated by Breeze2 software and Prism was used for graphing.

The formation of intracellular amyloid aggregates in thoracic adipose tissue and brain glia in ATTR models of the fruit fly results in an abnormal wing posture and motor defects (41-43). Several ATTR models are available to be tested in flies; here, the focus was on flies carrying the TTR familial mutant V30M (43) (abbreviated TTRV30M), and the amyloidogenic mutant V14N/V16E (41) (abbreviated TTR-A). Transgenic lines were generated in the w1118 strain. Two transgenes for the human TTR gene UAS-TTRV30M and UAS-TTRV14N/V16E (abbreviated UAS-TTR-A) were expressed under control of pan-neuronal GAL4 driver (nSyb-GAL4) to drive expression in all types of post-mitotic neurons. Genotypes: w; +; UAS-TTRV30M/nSyb-GAL4 (43), or w; +; UAS-TTRV14N/V16E/nSyb-GAL4 (41); wild type Oregon R strain was obtained from *Drosophila* Bloomington Stock Center (BDSC #6361, Indiana University) and used as healthy controls in crosses with the nSyb-GAL4 driver line (w; +; +/nSyb-GAL4).

Flies were kept at 60% humidity at 20° C. under a 12:12 hour light:dark cycle (8 a.m. to 8 p.m. daily) until fly eclosion and at 29° C. post eclosion. This temperature shift was adopted to lower the expression of nSyb-GAL4 driver during development before adding the tested compounds.

The crossings were reared in bottles containing standard *Drosophila* food (corn meal, corn syrup solids, yeast, water and agar). Newly eclosed female flies (10 flies per vial) were transferred into 5 ml ventilated vials (75×13 mm, polystyrene tubes with archiving caps with filter, Sarstedt, Nümbrecht, Germany), containing low-melt fly food and tested compounds according to the formula developed by Markstein et al. for mixing drugs in low volumes (84). Briefly, the food was prepared with distilled water containing 2% (w/v) autoclaved yeast, 7% (v/v) corn syrup liquids, and 1.5% (w/v) agarose (composed of 1 part standard agarose to 11 parts low-melt agarose). The food was mixed as a liquid with drugs at 37° C. The resulting food and compound mixtures solidified at 30° C. into soft fly edible gels. All peptides were dissolved in 0.22 μm filtered water, first to 5 mM stock solution. These working solutions were further diluted in fly food prior to use to final concentration: 100 μM or 300 μM. Flies were fed compounds present in fly food after adult flies enclosure (developmental stages excluded) until death. Fresh food containing the compounds was changed every second or third day and the number of dead flies was recorded.

Flies were fed with food and compound mixtures, containing vehicle, 300 μM or 2.5 mM of peptide cocktails, for 3 days. Flies were snap-frozen before heads and bodies were separated and stored. Samples containing 30 heads or bodies were spiked with the internal standards IS-F: RRRRH-VAHPFVEFTE (SEQ ID NO: 67) and IS-H: RRRRSYVTNPTSYTV (SEQ ID NO: 68) (250 pmoles each in 25 μl of water) to which was added water/methanol (500 μl, 1/1, v/v) and trifluoroacetic acid (TFA, 100 μl). The samples were homogenized with a rotor/stator apparatus (PT 3100 Polygon) at 50% maximal speed for 1-2 minutes after which they were centrifuged at 16,000×g for 5 min at room temperature. The supernatants were transferred to clean microcentrifuge tubes and dried in a vacuum centrifuge. 50 μl water was added to the dried residues, and after vigorous mixing and sonication in a bath sonicator for 15 min they were centrifuged at 16,000×g for 5 min at room temperature and the supernatants were transferred to HPLC injector vials. With each batch of samples a series of standards were prepared in which TabF1, TabH1, TabF2 and TabH2 peptides (0, 0.1, 0.25, 0.5, and 1.0 nmol) in duplicate were prepared as above with the internal standards (250 pmoles) in water/methanol (500 μl, 1/1, v/v) and trifluoroacetic acid (TFA, 100 μl). These samples were processed as described above.

Peptides were detected by combined liquid chromatography-tandem mass spectrometry with selected ion monitoring (SIM). Aliquots of the final samples (20 μl) were injected onto a reverse phase HPLC column (Phenomenex Kinetex C18, 1.7μ☐☐ 100×2.1 mm) equilibrated in eluent A (water/formic acid, 100/0.1, v/v) and eluted (100 μl/min) with a linearly increasing concentration of eluent B (acetonitrile/formic acid, 100/0.1, v/v: min/% B; 0/0, 5/0, 25/100, 28/0, and 35/0). The effluent from the column was directed to an electrospray ion source (Agilent Jet Stream) connected to a triple quadrupole mass spectrometer (Agilent 6460) set to selectively ion monitor (SIM) the triply-charged parent ions for each peptide using previously optimized source conditions and with instrument manufacturer-supplied software (Agilent Mass Hunter: IS-H, m/z 643.2 at retention time (rt) 12.19 min; IS-F, m/z 646.5 at rt 12.81 min; TabH1, m/z 647.9 at rt 11.92 min; TabH2, m/z 647.9 at rt 12.26 min; TabF1, m/z 651.1 at rt 12.35 min; TabF2, m/z 651.1 at rt 13.11 min). The areas of each peak were integrated and recorded. A standard curve constructed from the data obtained from the standards in which the ratio of peptide peak area/internal standard peak area was plotted against the amount of peptide in each standard. The amount of each peptide in the samples was then derived by interpolation from the standard curve.

All females flies were pooled and randomized. Ten flies of each genotype or drug treatment were placed in plastic vials in replicates, gently tapped down to the bottom and allowed to climb. Several motor skills were analyzed in a climbing assay at various time points along with survival analysis. (i) Mean distance or mean length of trajectories corresponding to one fly in a vial in mm. (ii) Mean velocity of 10 flies moving in one vial in mm/s. (iii) Motion represents percentage of flies being in movement in one vial. A fly is considered in movement when its velocity is equal or higher than 2.5 mm/s. (iv) Maximum velocity of flies moving in one vial in mm/s. (v) Mean length of trajectory among all detected flies in one vial in mm. (vi) Total distance or the sum of all trajectory lengths in one vial in mm. Recordings of ten second fly movements were acquired in duplicates and analyzed with FlyTracker hardware and software (commercially available from Airoptics Sp. z o.o., Poland). Analysis was performed in real time and the data were analyzed again in the offline mode.

For every condition, 20 heads were homogenized in 100 μl Triton X-100 buffer (1% Triton X-100, 1x PBS, pH 7,6) containing a protease inhibitor cocktail (general use, Amresco) on ice. Samples were mixed gently and centrifuged for 20 minutes at 15,000×g at 4° C. This process was done twice and the supernatant was collected and saved as soluble fraction (SF). The pellet was resuspended in 100 μl of 50 mM Tris pH 7,6, 4% SDS, gently vortexed and saved as insoluble fraction (IF). Both SF and IF samples were boiled separately for 10 minutes. Samples were sonicated for 10 minutes and centrifuged at 15,000×g at room temperature for 10 minutes. Both supernatants were collected and saved (SF-S1 and IF-S1, respectively). The pellet resultant from SF was resuspended in 100 μl of 50 mM Tris pH 7,6, 4% SDS (SF-P1). The pellet resultant from IF was resuspended in 50 μl of 50 mM Tris-HCl pH 7,6, 175 mM NaCl, 5 mM EDTA, 5% SDS, 8 M urea, and vortexed for 1.5 hours (IF-P1). SF-S1 and SF-P1 were mixed and loaded together. IF-S1 and IF-P1 were mixed and loaded together. 4xLDS sample buffer and DTT containing (10×) Sample Reducing Agent (ThermoFisher Scientific) were added to the samples. Samples were boiled for 20 minutes before electrophoresis. Total protein concentration was estimated with Pierce™ BCA Protein Assay Kit—Reducing Agent Compatible (ThermoFisher Scientific). For each treatment 2.2 μg protein was resolved on NuPAGE® Novex® 4-12% Bis-Tris Protein Gels in MES SDS running buffer and electroblotted onto a nitrocellulose membrane using iBlot2 gel transfer device (ThermoFisher Scientific). All steps were performed according to the manufacturer. The primary antibodies used were rabbit polyclonal against human TTR 1:2,000 (DAKO). Detection was performed with Western Breeze Chromogenic kit for Rabbit Primary Antibodies. Transthyretin levels from four independent blots were quantified with Gel-Doc XR+ Imager and Image Lab 5.2 software (Bio-Rad). Recombinant TTR wild type protein standard was used to calculate absolute levels of TTR immunodetected on blots.

Statistical analysis of absorbance, TTR aggregation, and Thioflavin T signal was performed with Prism 7 for Mac (GraphPad Software) using unpaired t test. Statistical analysis of fly survival was performed with IBM SPSS Statistics 20 for Windows (IBM Corporation). Survival data were analyzed with the Kaplan-Meier method, and statistical comparisons were made with Log rank pair-wise comparisons. Additionally, Cox Regression analysis was performed to estimate hazard coefficient for each treatment. Statistical analysis of motor skills under various treatments was performed with IBM SPSS Statistics 20 for Windows (IBM Corporation). Statistical significance for locomotor effects was determined by General Linear Model multivariate analysis of variance (Multivariate GLM, also known as MANOVA), followed by Fisher's post hoc. All samples and animals were included in the analysis. The mean difference was considered to be statistically significant at 95% confidence interval. All quantitative experiments are presented as means±S.D. or means±S.E.M. (as indicated) of at least three independent experiments (as indicated). No statistical methods were used to predetermine sample size before analysis. The experiments were randomized. Vials were coded and investigators were blinded to allocations both during readouts and outcome assessment.

REFERENCES

Note: This application references a number of different publications as indicated throughout the specification by reference numbers enclosed in brackets, e.g., [x]. A list of these different publications ordered according to these reference numbers can be found below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

1. P. P. Costa, A. S. Figueira, F. R. Bravo, Amyloid fibril protein related to prealbumin in familial amyloidotic polyneuropathy. *Proc Natl Acad Sci USA* 75, 4499 (1978).
2. K. Sletten, P. Westermark, J. B. Natvig, Senile cardiac amyloid is related to prealbumin. *Scand J Immunol* 12, 503 (1980).
3. M. D. Benson, Partial amino acid sequence homology between an heredofamilial amyloid protein and human plasma prealbumin. *J Clin Invest* 67, 1035 (1981).
4. M. Pras, F. Prelli, E. C. Franklin, B. Frangione, Primary structure of an amyloid prealbumin variant in familial polyneuropathy of Jewish origin. *Proc Natl Acad Sci USA* 80, 539 (1983).
5. A. R. Hurshman Babbes, E. T. Powers, J. W. Kelly, Quantification of the thermodynamically linked quaternary and tertiary structural stabilities of transthyretin and its disease-associated variants: the relationship between stability and amyloidosis. *Biochemistry* 47, 6969 (2008).
6. M. D. Benson, Pathogenesis of transthyretin amyloidosis. *Amyloid* 19 Suppl 1, 14 (2012).
7. P. D. Gorevic, F. C. Prelli, J. Wright, M. Pras, B. Frangione, Systemic senile amyloidosis. Identification of a new prealbumin (transthyretin) variant in cardiac tissue: immunologic and biochemical similarity to one form of familial amyloidotic polyneuropathy. *J Clin Invest* 83, 836 (1989).
8. P. Westermark, J. Bergstrom, A. Solomon, C. Murphy, K. Sletten, Transthyretin-derived senile systemic amyloidosis: clinicopathologic and structural considerations. *Amyloid* 10 Suppl 1, 48 (2003).
9. Y. Su, Y. Horibata, M. Ueda, M. Tasaki, Y. Misumi, J. Guo, M. Shono, H. Jono, K. Obayashi, H. Ogawa, Y. Ando, Transthyretin-derived amyloid deposition in the heart of an elderly Japanese population. *Amyloid* 18 Suppl 1, 180 (2011).
10. E. Ihse, O. B. Suhr, U. Hellman, P. Westermark, Variation in amount of wild-type transthyretin in different fibril and tissue types in ATTR amyloidosis. *J Mol Med (Berl)* 89, 171 (2011).
11. J. Bergstrom, A. Gustaysson, U. Hellman, K. Sletten, C. L. Murphy, D. T. Weiss, A. Solomon, B. O. Olofsson, P. Westermark, Amyloid deposits in transthyretin-derived amyloidosis: cleaved transthyretin is associated with distinct amyloid morphology. *J Pathol* 206, 224 (2005).
12. M. D. Benson, in *The Hereditary Amyloidoses*, Picken, M.M., A. Dogan, G. A. Herrera, Eds. (Humana Press, 2012), pp. 53-67.
13. M. D. Benson, Liver transplantation and transthyretin amyloidosis. *Muscle Nerve* 47, 157 (2013).
14. E. A. Pomfret, W. D. Lewis, R. L. Jenkins, P. Bergethon, S. W. Dubrey, J. Reisinger, R. H. Falk, M. Skinner, Effect of orthotopic liver transplantation on the progression of familial amyloidotic polyneuropathy. *Transplantation* 65, 918 (1998).
15. A. J. Stangou, P. N. Hawkins, N. D. Heaton, M. Rela, M. Monaghan, P. Nihoyannopoulos, J. O'Grady, M. B. Pepys, R. Williams, Progressive cardiac amyloidosis following liver transplantation for familial amyloid polyneuropathy: implications for amyloid fibrillogenesis. *Transplantation* 66, 229 (1998).
16. M. Yazaki, T. Tokuda, A. Nakamura, T. Higashikata, J. Koyama, K. Higuchi, Y. Harihara, S. Baba, F. Kametani, S. Ikeda, Cardiac amyloid in patients with familial amyloid polyneuropathy consists of abundant wild-type transthyretin. *Biochem Biophys Res Commun* 274, 702 (2000).
17. A. J. Stangou, P. N. Hawkins, Liver transplantation in transthyretin-related familial amyloid polyneuropathy. *Curr Opin Neurol* 17, 615 (2004).
18. T. R. Foss, R. L. Wiseman, J. W. Kelly, The pathway by which the tetrameric protein transthyretin dissociates. *Biochemistry* 44, 15525 (2005).
19. A. Nordlund, M. Oliveberg, Folding of Cu/Zn superoxide dismutase suggests structural hotspots for gain of neurotoxic function in ALS: parallels to precursors in amyloid disease. *Proc Natl Acad Sci USA* 103, 10218 (2006).
20. J. N. Buxbaum, The systemic amyloidoses. *Curr Opin Rheumatol* 16, 67 (2004).
21. B. Brumshtein, S. R. Esswein, L. Salwinski, M. L. Phillips, A. T. Ly, D. Cascio, M. R. Sawaya, D. S. Eisenberg, Inhibition by small-molecule ligands of formation of amyloid fibrils of an immunoglobulin light chain variable domain. *Elife* 4, e10935 (2015).
22. C. Carazzone, R. Colombo, M. Quaglia, P. Mangione, S. Raimondi, S. Giorgetti, G. Caccialanza, V. Bellotti, E. De Lorenzi, Sulfonated molecules that bind a partially structured species of beta2-microglobulin also influence refolding and fibrillogenesis. *Electrophoresis* 29, 1502 (2008).
23. P. Hammarstrom, R. L. Wiseman, E. T. Powers, J. W. Kelly, Prevention of transthyretin amyloid disease by changing protein misfolding energetics. *Science* 299, 713 (2003).

24. G. J. Miroy, Z. Lai, H. A. Lashuel, S. A. Peterson, C. Strang, J. W. Kelly, Inhibiting transthyretin amyloid fibril formation via protein stabilization. Proc *Natl Acad Sci USA* 93, 15051 (1996).

25. C. E. Bulawa, S. Connelly, M. Devit, L. Wang, C. Weigel, J. A. Fleming, J. Packman, E. T. Powers, R. L. Wiseman, T. R. Foss, I. A. Wilson, J. W. Kelly, R. Labaudiniere, Tafamidis, a potent and selective transthyretin kinetic stabilizer that inhibits the amyloid cascade. *Proc Natl Acad Sci USA* 109, 9629 (2012).

26. M. Waddington Cruz, M. D. Benson, A Review of Tafamidis for the Treatment of Transthyretin-Related Amyloidosis. *Neurol Ther* 4, 61 (2015).

27. M. Waddington Cruz, L. Amass, D. Keohane, J. Schwartz, H. Li, B. Gundapaneni, Early intervention with tafamidis provides long-term (5.5-year) delay of neurologic progression in transthyretin hereditary amyloid polyneuropathy. *Amyloid* 23, 178 (2016).

28. P. Lozeron, M. Theaudin, Z. Mincheva, B. Ducot, C. Lacroix, D. Adams, Effect on disability and safety of Tafamidis in late onset of Met30 transthyretin familial amyloid polyneuropathy. *Eur J Neurol* 20, 1539 (2013).

29. V. Plante-Bordeneuve, F. Gorram, H. Salhi, T. Nordine, S. S. Ayache, P. Le Corvoisier, D. Azoulay, C. Feray, T. Damy, J. P. Lefaucheur, Long-term treatment of transthyretin familial amyloid polyneuropathy with tafamidis: a clinical and neurophysiological study. *J Neurol* 264, 268 (2017).

30. T. Fujita, T. Inomata, T. Kaida, Y. Iida, Y. Ikeda, T. Nabeta, S. Ishii, E. Maekawa, T. Naruke, T. Koitabashi, E. Kitamura, Y. Sekijima, J. Ako, Tafamidis for the Treatment of Hereditary Transthyretin Amyloid Cardiomyopathy: A Case Report. *Cardiology* 137, 74 (2017).

31. D. Eisenberg, M. Jucker, The amyloid state of proteins in human diseases. Cell 148, 1188 (2012).

32. L. Saelices, L. M. Johnson, W. Y. Liang, M. R. Sawaya, D. Cascio, P. Ruchala, J. Whitelegge, L. Jiang, R. Riek, D. S. Eisenberg, Uncovering the Mechanism of Aggregation of Human Transthyretin. *J Biol Chem* 290, 28932 (2015).

33. R. Nelson, M. R. Sawaya, M. Balbirnie, A. O. Madsen, C. Riekel, R. Grothe, D. Eisenberg, Structure of the cross-beta spine of amyloid-like fibrils. *Nature* 435, 773 (2005).

34. P. Westermark, K. Steffen, B. Johansson, G. G. Cornwell, Fibril in senile systemic amyloidosis is derived from normal transthyretin. *Proc Natl Acad Sci USA* 87, 2843 (1990).

35. N. J. Galant, P. Westermark, J. N. Higaki, A. Chakrabartty, Transthyretin amyloidosis: an under-recognized neuropathy and cardiomyopathy. *Clin Sci* (Load) 131, 395 (2017).

36. T. Damy, M. S. Maurer, C. Rapezzi, V. Plante-Bordeneuve, O. N. Karayal, R. Mundayat, O. B. Suhr, A. V. Kristen, Clinical, ECG and echocardiographic clues to the diagnosis of TTR-related cardiomyopathy. *Open Heart* 3, e000289 (2016).

37. C. Rapezzi, C. C. Quarta, L. Obici, F. Perfetto, S. Longhi, F. Salvi, E. Biagini, M. Lorenzini, F. Grigioni, O. Leone, F. Cappelli, G. Palladini, P. Rimessi, A. Ferlini, G. Arpesella, A. D. Pinna, G. Merlini, S. Perlini, Disease profile and differential diagnosis of hereditary transthyretin-related amyloidosis with exclusively cardiac phenotype: an Italian perspective. *Eur Heart J* 34, 520 (2013).

38. W. Colon, J. W. Kelly, Partial denaturation of transthyretin is sufficient for amyloid fibril formation in vitro. *Biochemistry* 31, 8654 (1992).

39. A. Castano, S. Helmke, J. Alvarez, S. Delisle, M. S. Maurer, Diflunisal for ATTR cardiac amyloidosis. *Congest Heart Fail* 18, 315 (2012).

40. T. Coelho, M. Carvalho, M. J. Saraiva, I. Alves, M. R. Almeida, P. P. Costa, A strikingly benign evolution of FAP in an individual found to be a compound heterozygote for two TTR mutations: TTR MET 30 and TTR MET 119. *J. Rheumatol.* 20, 179 (1993).

41. M. Pokrzywa, I. Dacklin, D. Hultmark, E. Lundgren, Misfolded transthyretin causes behavioral changes in a *Drosophila* model for transthyretin-associated amyloidosis. *Eur J Neurosci* 26, 913 (2007).

42. M. Pokrzywa, I. Dacklin, M. Vestling, D. Hultmark, E. Lundgren, R. Cantera, Uptake of aggregating transthyretin by fat body in a *Drosophila* model for TTR-associated amyloidosis. *PLoS One* 5, e14343 (2010).

43. I. Iakovleva, A. Begum, M. Pokrzywa, M. Walfridsson, A. E. Sauer-Eriksson, A. Olofsson, The flavonoid luteolin, but not luteolin-7-O-glucoside, prevents a transthyretin mediated toxic response. *PLoS One* 10, e0128222 (2015).

44. J. T. Jarrett, P. T. J. Lansbury, Seeding "one-dimensional crystallization" of amyloid: a pathogenic mechanism in Alzheimer's disease and scrapie? *Cell* 73, 1055 (1993).

45. P. Arosio, T. P. Knowles, S. Linse, On the lag phase in amyloid fibril formation. *Phys Chem Chem Phys* 17, 7606 (2015).

46. J. J. Liepnieks, M. D. Benson, Progression of cardiac amyloid deposition in hereditary transthyretin amyloidosis patients after liver transplantation. *Amyloid* 14, 277 (2007).

47. A. Carvalho, A. Rocha, L. Lobato, Liver transplantation in transthyretin amyloidosis: issues and challenges. *Liver Transpl* 21, 282 (2015).

48. L. Llado, C. Baliellas, C. Casasnovas, I. Ferrer, J. Fabregat, E. Ramos, J. Castellote, J. Torras, X. Xiol, A. Rafecas, Risk of transmission of systemic transthyretin amyloidosis after domino liver transplantation. *Liver Transpl* 16, 1386 (2010).

49. Y. Misumi, Y. Narita, T. Oshima, M. Ueda, T. Yamashita, M. Tasaki, K. Obayashi, K. Isono, Y. Inomata, Y. Ando, Recipient aging accelerates acquired transthyretin amyloidosis after domino liver transplantation. *Liver Transpl* 22, 656 (2016).

50. J. N. Buxbaum, C. Tagoe, G. Gallo, J. R. Walker, S. Kurian, D. R. Salomon, Why are some amyloidoses systemic? Does hepatic "chaperoning at a distance" prevent cardiac deposition in a transgenic model of human senile systemic (transthyretin) amyloidosis. *FASEB J* 26, 2283 (2012).

51. G. T. Westermark, P. Westermark, Prion-like aggregates: infectious agents in human disease. *Trends Mol Med* 16, 501 (2010).

52. T. Yoshinaga, M. Yazaki, Y. Sekijima, F. Kametani, K. Miyashita, N. Hachiya, T. Tanaka, N. Kokudo, K. Higuchi, S. Ikeda, The pathological and biochemical identification of possible seed-lesions of transmitted transthyretin amyloidosis after domino liver transplantation. *J Pathol Clin Res* 2, 72 (2016).

53. K. Obayashi, M. Ueda, H. Jono, T. Yamashita, M. Yazaki, F. Kametani, Y. Ohya, Y. Inomata, S. Ikeda, Y. Ando, Amyloid turnover after liver transplantation in FAP. *Amyloid* 18 Suppl 1, 187 (2011).

54. T. Coelho, L. F. Maia, A. Martins da Silva, M. Waddington Cruz, V. Plante-Bordeneuve, P. Lozeron, O. B. Suhr, J. M. Campistol, I. M. Conceicao, H. H. Schmidt, P. Trigo, J. W. Kelly, R. Labaudiniere, J. Chan, J. Packman, A. Wilson, D. R. Grogan, Tafamidis for transthyretin familial amyloid polyneuropathy: a randomized, controlled trial. *Neurology* 79, 785 (2012).
55. L. Obici, G. Merlini, An overview of drugs currently under investigation for the treatment of transthyretin-related hereditary amyloidosis. *Expert Opin Investig Drugs* 23, 1239 (2014).
56. J. L. Berk, O. B. Suhr, L. Obici, Y. Sekijima, S. R. Zeldenrust, T. Yamashita, M. A. Heneghan, P. D. Gorevic, W. J. Litchy, J. F. Wiesman, E. Nordh, M. Corato, A. Lozza, A. Cortese, J. Robinson-Papp, T. Colton, D. V. Rybin, A. B. Bisbee, Y. Ando, S. Ikeda, D. C. Seldin, G. Merlini, M. Skinner, J. W. Kelly, P. J. Dyck, T. C. Diflunisal, Repurposing diflunisal for familial amyloid polyneuropathy: a randomized clinical trial. *JAMA* 4 310, 2658 (2013).
57. Y. Sekijima, K. Tojo, H. Morita, J. Koyama, S. Ikeda, Safety and efficacy of long-term diflunisal administration in hereditary transthyretin (ATTR) amyloidosis. *Amyloid* 22, 79 (2015).
58. S. L. Adamski-Werner, S. K. Palaninathan, J. C. Sacchettini, J. W. Kelly, Diflunisal analogues stabilize the native state of transthyretin. Potent inhibition of amyloidogenesis. *J Med Chem* 47, 355 (2004).
59. A. R. Hurshman, J. T. White, E. T. Powers, J. W. Kelly, Transthyretin aggregation under partially denaturing conditions is a downhill polymerization. *Biochemistry* 43, 7365 (2004).
60. S. L. McCutchen, Z. Lai, G. J. Miroy, J. W. Kelly, W. Colon, Comparison of lethal and nonlethal transthyretin variants and their relationship to amyloid disease. *Biochemistry* 34, 13527 (1995).
61. S. A. Sievers, J. Karanicolas, H. W. Chang, A. Zhao, L. Jiang, O. Zirafi, J. T. Stevens, J. Munch, D. Baker, D. Eisenberg, Structure-based design of non-natural amino-acid inhibitors of amyloid fibril formation. *Nature* 475, 96 (2011).
62. A. Soragni, D. M. Janzen, L. M. Johnson, A. G. Lindgren, A. Thai-Quynh Nguyen, E. Tiourin, A. B. Soriaga, J. Lu, L. Jiang, K. F. Faull, M. Pellegrini, S. Memarzadeh, D. S. Eisenberg, A Designed Inhibitor of p53 Aggregation Rescues p53 Tumor Suppression in Ovarian Carcinomas. *Cancer Cell* 29, 90 (2016).
63. R. Kisilevsky, M. Axelrad, The pathogenesis of amyloid deposition: a new hypothesis. *Med Hypotheses* 2, 233 (1976).
64. R. Kisilevsky, M. Axelrad, W. Corbett, S. Brunet, F. Scott, The role of inflammatory cells in the pathogenesis of amyloidosis. *Lab Invest* 37, 544 (1977).
65. R. Kisilevsky, L. Boudreau, Kinetics of amyloid deposition. I. The effects of amyloid-enhancing factor and splenectomy. *Lab Invest* 48, 53 (1983).
66. M. A. Axelrad, R. Kisilevsky, J. Willmer, S. J. Chen, M. Skinner, Further characterization of amyloid-enhancing factor. *Lab Invest* 47, 139 (1982).
67. E. J. Ackermann, S. Guo, M. D. Benson, S. Booten, S. Freier, S. G. Hughes, T. W. Kim, T. Jesse Kwoh, J. Matson, D. Norris, R. Yu, A. Watt, B. P. Monia, Suppressing transthyretin production in mice, monkeys and humans using 2nd-Generation antisense oligonucleotides. *Amyloid* 23, 148 (2016).
68. E. J. Ackermann, S. Guo, S. Booten, L. Alvarado, M. Benson, S. Hughes, B. P. Monia, Clinical development of an antisense therapy for the treatment of transthyretin-associated polyneuropathy. *Amyloid* 19 Suppl 1, 43 (2012).
69. T. Coelho, D. Adams, A. Silva, P. Lozeron, P. N. Hawkins, T. Mant, J. Perez, J. Chiesa, S. Warrington, E. Tranter, M. Munisamy, R. Falzone, J. Harrop, J. Cehelsky, B. R. Bettencourt, M. Geissler, J. S. Butler, A. Sehgal, R. E. Meyers, Q. Chen, T. Borland, R. M. Hutabarat, V. A. Clausen, R. Alvarez, K. Fitzgerald, C. Gamba-Vitalo, S. V. Nochur, A. K. Vaishnaw, D. W. Sah, J. A. Gollob, O. B. Suhr, Safety and efficacy of RNAi therapy for transthyretin amyloidosis. *N Engl J Med* 369, 819 (2013).
70. J. N. Higaki, A. Chakrabartty, N. J. Galant, K. C. Hadley, B. Hammerson, T. Nijjar, R. Torres, J. R. Tapia, J. Salmans, R. Barbour, S. J. Tam, K. Flanagan, W. Zago, G. G. Kinney, Novel conformation-specific monoclonal antibodies against amyloidogenic forms of transthyretin. *Amyloid* 23, 86 (2016).
71. A. Hosoi, Y. Su, M. Torikai, H. Jono, D. Ishikawa, K. Soejima, H. Higuchi, J. Guo, M. Ueda, G. Suenaga, H. Motokawa, T. Ikeda, S. Senju, T. Nakashima, Y. Ando, Novel Antibody for the Treatment of Transthyretin Amyloidosis. *J Biol Chem* (2016).
72. E. Ihse, C. Rapezzi, G. Merlini, M. D. Benson, Y. Ando, O. B. Suhr, S. Ikeda, F. Lavatelli, L. Obici, C. C. Quarta, O. Leone, H. Jono, M. Ueda, M. Lorenzini, J. Liepnieks, T. Ohshima, M. Tasaki, T. Yamashita, P. Westermark, Amyloid fibrils containing fragmented ATTR may be the standard fibril composition in ATTR amyloidosis. *Amyloid* 20, 142 (2013).
73. B. P. Hazenberg, P. C. Limburg, J. Bijzet, M. H. van Rijswijk, A quantitative method for detecting deposits of amyloid A protein in aspirated fat tissue of patients with arthritis. *Ann Rheum Dis* 58, 96 (1999).
74. H. Puchtler, F. Sweat, M. Levine, On the binding of Congo red by amyloid. *J Histochem Cytochem* 10, 355-363 (1962).
75. J. A. Rodriguez, M. I. Ivanova, M. R. Sawaya, D. Cascio, F. E. Reyes, D. Shi, S. Sangwan, E. L. Guenther, L. M. Johnson, M. Zhang, L. Jiang, M. A. Arbing, B. L. Nannenga, J. Hattne, J. Whitelegge, A. S. Brewster, M. Messerschmidt, S. Boutet, N. K. Sauter, T. Gonen, D. S. Eisenberg, Structure of the toxic core of alpha-synuclein from invisible crystals. *Nature* 525, 486 (2015).
76. A. Arvai, http://www.scripps.edu/tainer/arvai/adxv.html (2015).
77. W. S. Rasband, U. S. ImageJ, http://imagej.nih.gov/ij/ (1997).
78. B. F. Shaw, H. L. Lelie, A. Durazo, A. M. Nersissian, G. Xu, P. K. Chan, E. B. Gralla, A. Tiwari, L. J. Hayward, D. R. Borchelt, J. S. Valentine, J. P. Whitelegge, Detergent-insoluble aggregates associated with amyotrophic lateral sclerosis in transgenic mice contain primarily full-length, unmodified superoxide dismutase-1. *J Biol Chem* 283, 8340 (2008).
79. J. Rappsilber, M. Mann, Y. Ishihama, Protocol for micro-purification, enrichment, pre-fractionation and storage of peptides for proteomics using StageTips. *Nat Protoc* 2, 1896 (2007).
80. A. Micsonai, F. Wien, L. Kernya, Y. H. Lee, Y. Goto, M. Refregiers, J. Kardos, Accurate secondary structure prediction and fold recognition for circular dichroism spectroscopy. *Proc Natl Acad Sci USA* 112, E3095 (2015).
81. M. Cruz, J. M. Tusell, D. Grillo-Bosch, F. Albericio, J. Serratosa, F. Rabanal, E. Giralt, Inhibition of beta-amyloid toxicity by short peptides containing N-methyl amino acids. *J Pept Res* 63, 324 (2004).
82. M. J. Thompson, S. A. Sievers, J. Karanicolas, M. I. Ivanova, D. Baker, D. Eisenberg, The 3D profile method for identifying fibril-forming segments of proteins. *Proc Natl Acad Sci USA* 103, 4074 (2006).

83. L. Goldschmidt, P. K. Teng, R. Riek, D. Eisenberg, Identifying the amylome, proteins capable of forming amyloid-like fibrils. *Proc Natl Acad Sci USA* 107, 3487 (2010).
84. M. Markstein, S. Dettorre, J. Cho, R. A. Neumuller, S. Craig-Muller, N. Perrimon, Systematic screen of chemotherapeutics in *Drosophila* stem cell tumors. *Proc Natl Acad Sci USA* 111, 4530 (2014).

SEQUENCES

TRANSTHYRETIN (e.g. GenBank: AAD45014.1)

MASHRLLLLCLAGLVFVSEAGPTGTGESKCPLMVKVLDAVRGSPAINVAV

HVFRKAADDTWEPFASGKTSESGELHGLTTEEEFVEGIYKVEIDTKSYWK

SEQUENCES -continued

ALGISPFHEHAEVVFTANDSGPRRYTIAALLSPYSYSTTAVVTNPKE (SEQ ID NO: 1)

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A pharmaceutical composition of matter comprising at least one peptide having the sequence:

PFHEHAEVVFTA; (SEQ ID NO: 2)

PYSYSTTAVVTN; (SEQ ID NO: 3)

HVAHPFVEFTE; (SEQ ID NO: 4)

SYVTNPTSYAVT; (SEQ ID NO: 5)

HFEVAFPVEHAT; (SEQ ID NO: 6)

YVSNPTSTYVAT; (SEQ ID NO: 7)
or

VANTSPTSYYVT; (SEQ ID NO: 8)

wherein:
at least one of the amino acids in the at least one peptide comprises an amino acid comprising a N-methyl group moiety; and/or
the at least one peptide is coupled to a heterologous peptide tag comprising a plurality of arginine (R) amino acids; and
a pharmaceutically acceptable carrier, wherein the pharmaceutically acceptable carrier comprises an agent that inhibits microbial growth.

2. The composition of claim 1, wherein the peptide is from 12 to 30 amino acids in length.

3. The composition of claim 1, wherein the composition comprises a plurality of peptides.

4. A method for reducing or inhibiting transthyretin (SEQ ID NO: 1) aggregation, comprising contacting transthyretin amyloid fibrils with at least one peptide comprising the sequence:

PFHEHAEVVFTA; (SEQ ID NO: 2)

PYSYSTTAVVTN; (SEQ ID NO: 3)

HVAHPFVEFTE; (SEQ ID NO: 4)

SYVTNPTSYAVT; (SEQ ID NO: 5)

HFEVAFPVEHAT; (SEQ ID NO: 6)

YVSNPTSTYVAT; (SEQ ID NO: 7)
or

VANTSPTSYYVT; (SEQ ID NO: 8)

wherein:
at least one of the amino acids in the at least one peptide comprises an amino acid comprising a N-methyl group moiety; and/or
the at least one peptide is coupled to a heterologous peptide tag comprising a plurality of arginine (R) amino acids;
in an amount sufficient to reduce or inhibit transthyretin aggregation, so that transthyretin (SEQ ID NO: 1) aggregation is reduced or inhibited.

5. The method of claim 4, wherein the transthyretin amyloid fibrils are within an in vivo environment.

6. A method of observing the presence or absence of transthyretin amyloid fibrils in a biological sample comprising:

(a) combining a biological sample with a peptide having the sequence:

PFHEHAEVVFTA; (SEQ ID NO: 2)

PYSYSTTAVVTN; (SEQ ID NO: 3)

HVAHPFVEFTE; (SEQ ID NO: 4)

SYVTNPTSYAVT; (SEQ ID NO: 5)

HFEVAFPVEHAT; (SEQ ID NO: 6)

YVSNPTSTYVAT; (SEQ ID NO: 7)
or

VANTSPTSYYVT (SEQ ID NO: 8)

(b) allowing the peptide to bind to transthyretin amyloid fibrils that may be present in the biological sample; and monitoring combination (b) for the presence of complexes formed between transthyretin amyloid fibrils and the peptide; wherein the presence of said complexes show the presence of transthyretin amyloid fibrils in the biological sample.

7. The method of claim 6, wherein the presence of complexes formed between transthyretin amyloid fibrils and the peptide is monitored using a detectable label that is coupled to the peptide.

8. The method of claim 7, wherein the detectable label comprises a heterologous peptide tag.

9. The method of claim 6, wherein the method is performed on a biological sample obtained from an individual suspected of suffering from wild-type or hereditary TTR amyloidosis.

* * * * *